United States Patent
Lafaquiere et al.

(10) Patent No.: US 11,920,178 B2
(45) Date of Patent: Mar. 5, 2024

(54) USE OF TYPE III POLYKETIDE SYNTHASES FROM BACTERIA AS PHLOROGLUCINOL SYNTHASES

(71) Applicant: COMPAGNIE GENERALE DES ETABLISSEMENTS MICHELIN, Clermont-Ferrand (FR)

(72) Inventors: Vincent Lafaquiere, Clermont-Ferrand (FR); Odile Ramaen, Ablis (FR); Dominique Louis, Forges les Bains (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 16/627,712

(22) PCT Filed: Jun. 29, 2018

(86) PCT No.: PCT/FR2018/051619
§ 371 (c)(1),
(2) Date: Dec. 30, 2019

(87) PCT Pub. No.: WO2019/002799
PCT Pub. Date: Jan. 3, 2019

(65) Prior Publication Data
US 2021/0147884 A1 May 20, 2021

(30) Foreign Application Priority Data
Jun. 30, 2017 (FR) ...................................... 1756106

(51) Int. Cl.
*C12P 7/22* (2006.01)
*C12N 9/10* (2006.01)

(52) U.S. Cl.
CPC .............. *C12P 7/22* (2013.01); *C12N 9/1029* (2013.01); *C12Y 203/01* (2013.01)

(58) Field of Classification Search
None
See application file for complete search history.

(56) References Cited

U.S. PATENT DOCUMENTS

| | | | |
|---|---|---|---|
| 10,179,921 B2 | 1/2019 | Delage et al. | |
| 2007/0178571 A1* | 8/2007 | Frost ...................... | C12N 15/52 435/193 |
| 2014/0315269 A1 | 10/2014 | Delage et al. | |

FOREIGN PATENT DOCUMENTS

WO 2012/003461 A2 1/2012

OTHER PUBLICATIONS

M.N. Mandryk-Litvinkovich et al. "Molecular Genetic Analysis of Determinants Defining Synthesis of 2,4-Diacetylphloroglucinol by Pseudomonas brassicacearum BIM B-446 Bacteria", Applied Biochemistry and Microbiology 53(1): 31-39 (Year: 2017).*
J.K. Patel et al. "Engineered production of 2,4-diacetylphloroglucinol in the diazotrophic endophytic bacterium Pseudomonas sp. WS5 and its beneficial effect in multiple plant-pathogen systems", Applied Soil Ecology 124:34-44 (Year: 2017).*
J. Almario et al. "Distribution of 2,4-Diacetylphloroglucinol Biosynthetic Genes Among Pseudomonas spp. Reveals Unexpected Polyphyleism", Frontiers in Microbiology 8: Article 1218 (Year: 2017).*
D. Yu et al. "Type III Polyketide Synthases in Natural Product Biosynthesis", IUBMB Life 64(4): 285-295 (Year: 2012).*
DeGroot et al. Uniprot Accession No. A0A1H1FBR5, Jun. 2017.*
J. Achkar et al., "Biosynthesis of Phloroglucinol," J. Am Chem Soc., vol. 127, pp. 5332-5333 (2005).
L. Meslet-Cladière et al., "Structure/Function Analysis of a Type III Polyketide Synthase in the Brown Alga Ectocarpus siliculosus Reveals a Biochemical Pathway in Phlorotannin Monomer Biosynthesis," The Plant Cell, vol. 25, pp. 3089-3103 (2013).
W. Zha et al., "Characterization of the Substrate Specificity of PhlD, a Type III Polyketide Synthase from Pseudomonas fluorescens," J. Biol Chem., vol. 281, No. 42, p. 32036-32047 (2006).
I. Abe et al., "Engineered Biosynthesis of Plant Polyketides: Chain Length Control in an Octaketide-Producing Plant Type III Polyketide Synthase," J. Am. Chem. Soc., vol. 127, pp. 12709-12716 (2005).
H. Baharum et al., "Molecular Cloning, Modeling, and Site-Directed Mutagenesis of Type III Polyketide Synthase from *Sargassum binderi* (Phaeophyta)," Marine Biotechnology, vol. 13, No. 5, pp. 845-856 (2011).
S. Sasso et al., "Microalgae in the postgenomic era: a blooming reservoir for new natural products," FEMS Microbiol. Rev., pp. 1-25 (2011).
Database UniProt XP002780083, "SubName: Full=Uncharacterized protein {ECO:0000313 | EMBL:EGB09027.1}", retrieved from EBI accession No. UniProt:F0Y6J5 (2011).
Database UniProt XP002780084, "SubName: Full=Type III polyketide synthase {ECO:0000313 | EMBL: ADK13089.1}", retrieved from EBI accession No. UniProt:D9J215 (2010).
Database EMBL XP002780085, "Sargassum binderi type III polyketide synthase mRNA, complete cds.", retrieved from EBI accession No. EM_STD:HM245964 (2010).
Database UniProt XP002780022, "SubName: Full=Long-chain alpha-pyrone synthase {ECO:0000313 | EMBL: SDQ98350.1}", retrieved from EBI accession No. UniProt:A0A1H1FBR5 (2017).
Database UniProt XP002780023, "SubName: Full=Polyketide synthase {ECO:0000313 | EMBL:KXP15269.1}", retrieved from EBI accession No. UniProt:A0A138AXW3 (2016).
Database UniProt XP002780024, "polyketide synthase [Tsukamurella tyrosinosolvens]", retrieved from NCBI accession No. RefSeq:WP_068743031.1 (2016).

(Continued)

*Primary Examiner* — Richard G Hutson
(74) *Attorney, Agent, or Firm* — VENABLE LLP

(57) ABSTRACT

The present invention relates to the use of type III polyketide synthases of bacteria, such as actinomycete bacteria, as phloroglucinol synthases. The present invention also relates to the isolated nucleic acid molecules encoding these type III polyketide synthases, and also to the vectors and the host cells comprising such nucleic acid molecules. The present invention also relates to methods for producing phloroglucinol.

20 Claims, 12 Drawing Sheets

Specification includes a Sequence Listing.

(56) References Cited

OTHER PUBLICATIONS

Co-pending U.S. Appl. No. 16/627,707, filed Jun. 29, 2018.
International Search Report dated Sep. 7, 2018, in corresponding PCT/FR2018/051619 (8 pages).
T. Siberfeld et al., "An Updated Classification of Brown Algae (Ochrophyta, Phaeophyceae)", Cryptogamie, Algologie, 35(2), pp. 117-156 (2014).
Extract from France Terme of French Ministry of Culture, http://www.culture.fr/franceterme/result?francetermeSearchTerme+cellule+h%C3%B4te&fracetermeSearchDomaine=0&francetermeSearchSubmit=search&action=search (2000).
Extract from Biology-online.org for "host cell" (2008), retrieved Jun. 8, 2021.
M. B. Austin, et al., "The chalcone synthase superfamily of type III polyketide synthases", Nat. Prod. Rep., vol. 20, pp. 79-110 (2003).
Y. Shimizu, et al., "Discriminating the reaction types of plant type III polyketide synthases", Bioinformatics, vol. 33, No. 13, pp. 1937-1943 (2017).
Polyketide synthase [Tsukamurella tyrosinosolvens], https://www.ncbi.nlm.nih.gov/protein/WP_068743031.?report=genpept (retrieved Jan. 18, 2022).
D. Yu et al., "Type III Polyketide Synthases in Natural Product Biosynthesis", Life, vol. 64, No. 4, pp. 285-295 (2012).
N. Funa et al., "A newpathway for polyketide synthesis in microorganisms", Nature, vol. 400, pp. 897-899 (1999).
N. Funa et al., "Alteration of reaction and substrate specificity of a bacterial type III polyketide synthase by site-directed mutagenesis", Biochem. J., vol. 367, pp. 781-789 (2002).
C. Taguchi et al., "Crystallization and preliminary X-ray diffraction studies of polyketide synthase-1 (PKS-1) from *Cannabis sativa*", Acta Cryst., F64, pp. 217-220 (2008).
NCBI Reference Sequence: WP_068567598.1 "polyketide synthase [Tsukamurella pulmonis]" Aug. 19, 2016.
UniProtKB-Q4K418 "Type III polyketide synthase PhID" Aug. 2, 2005.
PIRSF000451 "type III polyketide synthase" 2023.
InterPro IPR011141 "InterPro IPR011141" 2023.
N. Funa, et al., "Properties and Substrate Specificity of RppA, a Chalcone Synthase-related Polyketide Synthase in Streptomyces griseus*". J. Bio. Chem., vol. 277, No. 7, pp. 4628-4635 (2002).
GENBANK Database Reference Sequence: WP_068567598.1 (retrieved from https://www.ncbi.nlm.nih.gov/protein/WP_068567598.1/ on Sep. 29, 2023).
GENBANK Database Reference Sequence: WP_011211464.1 (retrieved from https://www.ncbi.nlm.nih.gov/protein/WP_011211464.1?report=genpept on Sep. 29, 2023).
GENBANK Database Reference Sequence: WP_012393954.1 (retrieved from https://www.ncbi.nlm.nih.gov/protein/WP_012393954.1 on Sep. 29, 2023).
GENBANK Database Reference Sequence: WP_013126955.1 (retrieved from https://www.ncbi.nlm.nih.gov/protein/WP_013126955.1 on Sep. 29, 2023).
GENBANK Database Reference Sequence:WP_019202763.1 (retrieved from https://www.ncbi.nlm.nih.gov/protein/WP_019202763.1 on Sep. 29, 2023).
GENBANK Database Reference Sequence: WP_023373103.1 (retrieved from https://www.ncbi.nlm.nih.gov/protein/WP_023373103.1 on Sep. 29, 2023).
GENBANK Database Reference Sequence: WP_031677738.1 (retrieved from https://www.ncbi.nlm.nih.gov/protein/WP_031677738 on Sep. 29, 2023).
GENBANK Database Reference Sequence: WP_066172590.1 (retrieved from https://www.ncbi.nlm.nih.gov/protein/WP_066172590.1?report-genpept on Sep. 29, 2023).
GENBANK Database Reference Sequence: WP_068525790.1 (retrieved from https://www.ncbi.nlm.nih.gov/protein/WP_068525790.1?report=genpept on Sep. 29, 2023).
GENBANK Database Reference Sequence: WP_068569959.1 (retrieved from https://www.ncbi.nlm.nih.gov/protein/WP_068569959.1?report-genpept on Sep. 29, 2023).

\* cited by examiner

Fig. 1

```
                                          10        20        30        40        50        60        70        80        90
                                          ....|....|....|....|....|....|....|....|....|....|....|....|....|....|....|....|....|....|
PhlD.Es [Ectocarpus siliculosu   MS------------------------------------XDEQTVPVIAGMAIGNPQYRCTQNEALAVASKCPGLESIKPVLERIYGNSRIGSRYF  60
PhlD.Tt [T. tyrosinosolvens]     MTMNAGSQGAPALDVPAPVLPAPG--TWLGAPPAPPTSVAVIESLATGSPAQTYGQAESADRVAARFDDPRQAERIRRVYAKTRVDERHL  88
PhlD.Tp [T. paurometabola]       --MIAPQIRLG--EPDTTPLPDP---LWHGAPPAPPTTVAVIESLATGSPAQAHGQSVSAERVAARFADPIQAERIRRVYANTAVATRHL  83
PhlD.Tps [T. pseudospumae]       ------------MAAPELPGTS--VWRGAPPAPPTSVAVIESLATGSPSQAYDQAESADRVASRFDDPRQAERIRRVYAKTRVAERHL   74
PhlD.Tpu [T. pulmonis]           ---MNTTEQ--------QSVLPQQ---AWLGAPPAPPTSVAVIESLATSSPTQTYGQAESADRVAARFDDPRQAERIRRVYAKTRVTERHL 77
PhlD.Tsp [T. sp. 1534]           ---MNIQDR--------STVAPDS---PALGFPPAPPTSVAVIESLATGSPSGVHAQAESADRVASRFDDPAQAERIRRVYTKTRVARRHL 77
PhlD.Nf [N. farcinica]           MSITVDEGGARPATEPRQRIHPDLGHAHTPMPRAPPVTIGVVEGIATGSPAQIVDQAEAAERVAALFTDPAQRARIARVYEKTRIETRRM  90
PhlD.Mma [M. marinum]            MSTAA-EGGAIRR--AGHEPRYDL----AQLPPAPPTTVAVIEGMATGAPQRVVAQADAAARVSELFVDPQQRERISRIYDKTRIDTRRM  83
PhlD.Mk [M. kansasii ATCC 1247   MSSAA-DGGAPVADVPGYEPHYDL----AQLPPAPPTTVAVIEGMATGVPQRVVRQSDAAARVAQMFVDPQQRERVSRVYAKTRIDTRRM  85
PhlD.Mt [M. tuberculosis]        MNVSA-ESGAPRR--AGQRHEVGL----AQLPPAPPTTVAVIEGLATGTPRRVVNQSDAADRVAELFLDPGQRERIPRVYQKSRITTRRM  83
PhlD.Gh [G. hydrophobica]        -----------------------------MPAPVTTVAVIEAVATGAPATVHPQTRAAEQVAELYDDPALQERIRRLYRNTRVQTRHL   59
```

Fig. 1 Continued

Fig. 3
Fig. 4A
| Gene | phloroglucinol mg.L$^{-1}$ | OD$_{600nm}$ | number of copies | Phloroglucinol /copy (mg.L$^{-1}$) |
|---|---|---|---|---|
| PHLD.Pf | 0 | 50 | 7 | 0 |
| PKS1.Es | 64 | 51 | 9 | 7 |
| PHLD.Tp | 430 | 36 | 6 | 71 |
| PHLD.Nf | 465 | 48 | 17 | 27 |
| PHLD.Mma | 380 | 41 | 17 | 22 |
| PHLD.Mk | 155 | 45 | 28 | 5 |
Fig. 4B
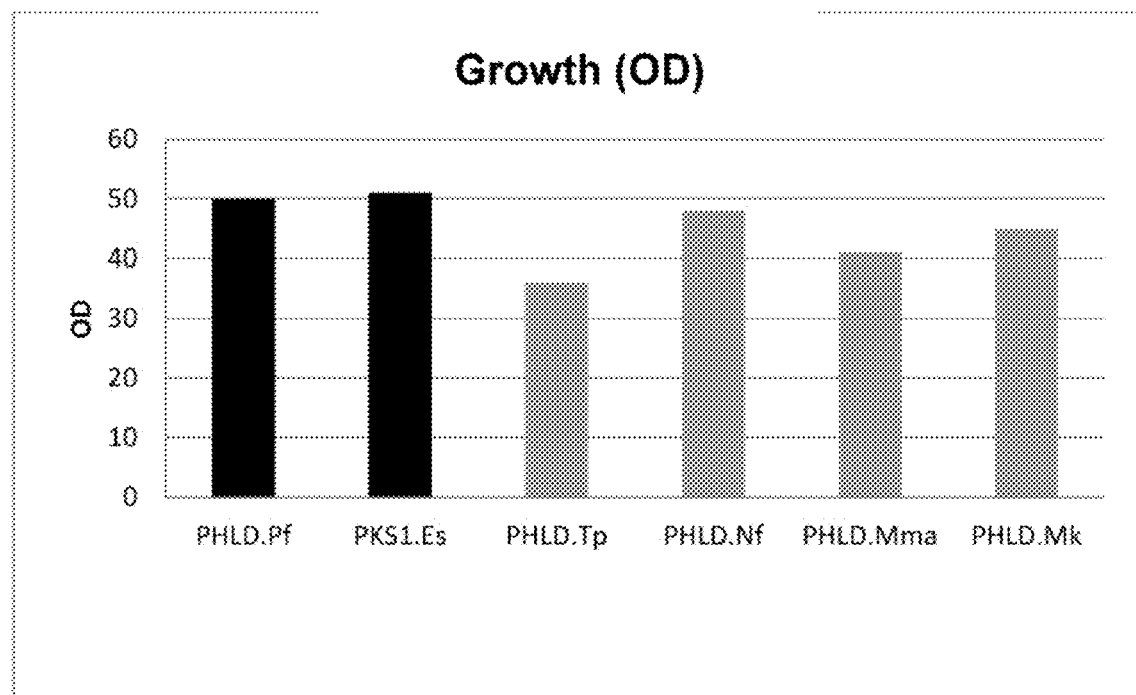

| PHLD | phloroglucinol mg.L⁻¹ | | OD 600nm | number of copies |
|---|---|---|---|---|
| | mean | standard deviation | | |
| pADH2-PHLD.Pf | 0.0 | 0.0 | 54 | 1 |
| pADH2-PKS1.Es | 2.7 | 1.0 | 57 | 1 |
| pADH2-PHLD.Tp | 86.0 | 16.0 | 56 | 1 |
| pADH2-PHLD.Tt | 220.0 | 6.0 | 59 | 1 |
| pADH2-PHLD.Tps | 41.0 | 2.2 | 55 | 1 |
| pADH2-PHLD.Tpu | 301.0 | 4.7 | 56 | 1 |
| pADH2-PHLD.Tsp | 131.0 | 5.6 | 56 | 1 |
| pADH2-PHLD.Nf | 40.0 | 7.2 | 54 | 1 |
| pADH2-PHLD.Mma | 49.6 | 9.7 | 58 | 1 |
| pADH2-PHLD.Mk | 6.0 | 0.5 | 57 | 1 |
| pADH2-PHLD.Mt | 17.5 | 11.0 | 51 | 1 |
| pADH2-PHLD.Gh | 24.8 | 6.7 | 59 | 1 |

| PHLD | phloroglucinol mg.L$^{-1}$ | | OD 600nm | PHLD gene copy number |
|---|---|---|---|---|
| | mean | standard deviation | | |
| pCCW12-PHLD.Pf | 0.0 | 0.0 | 57 | 1 |
| pCCW12-PKS1.Es | 8.4 | 2.7 | 57 | 1 |
| pCCW12-PHLD.Tp | 88.4 | 10.7 | 67 | 1 |
| pCCW12-PHLD.Tt | 340.3 | 28.0 | 63 | 1 |
| pCCW12-PHLD.Tps | 83.0 | 2.2 | 56 | 1 |
| pCCW12-PHLD.Tpu | 392.0 | 4.7 | 56 | 1 |
| pCCW12-PHLD.Tsp | 131.0 | 5.6 | 58 | 1 |
| pCCW12-PHLD.Nf | 11.4 | 3.5 | 61 | 1 |
| pCCW12-PHLD.Mma | 54.0 | 28.2 | 57 | 1 |
| pCCW12-PHLD.Mk | 5 | 0.5 | 56 | 1 |
| pCCW12-PHLD.Mt | 15.9 | 8.1 | 60 | 1 |
| pCCW12-PHLD.Gh | 31.6 | 18.4 | 57 | 1 |

SEQUENCE LISTING

```
<160> NUMBER OF SEQ ID NOS: 15

<210> SEQ ID NO 1
<211> LENGTH: 393
<212> TYPE: PRT
<213> ORGANISM: Tsukamurella paurometabola

<400> SEQUENCE: 1

Met Ile Ala Pro Gln Ile Arg Leu Gly Glu Pro Asp Thr Thr Pro Leu
1               5                   10                  15

Pro Asp Pro Leu Trp His Gly Ala Pro Pro Ala Pro Pro Thr Thr Val
            20                  25                  30

Ala Val Ile Glu Ser Leu Ala Thr Gly Ser Pro Ala Gln Ala His Gly
```

```
            35                  40                  45
Gln Ser Val Ser Ala Glu Arg Val Ala Arg Phe Ala Asp Pro Ile
 50                  55                  60

Gln Ala Glu Arg Ile Arg Arg Val Tyr Ala Asn Thr Ala Val Ala Thr
 65                  70                  75                  80

Arg His Leu Ala Ile Asp Pro Leu Ser Asp Phe Ala Asp Phe Ser
                 85                  90                  95

Ala Arg Pro Asp Thr Ile Arg Gln Arg Met Asp Leu Tyr Phe Glu His
                100                 105                 110

Ala Ala Pro Leu Ala Ile Glu Thr Ala Arg Arg Ala Leu Gly Ala Val
                115                 120                 125

Asp Ala Thr Glu Val Gly Gln Leu Ile Phe Val Thr Ser Thr Gly Phe
                130                 135                 140

Leu Ala Pro Gly Val Asp Val Ala Val Thr Arg Ser Leu Gly Leu Pro
145                 150                 155                 160

Ala Ser Thr Ser Arg Val Val Ile Asn Phe Met Gly Cys Ala Ala Ala
                165                 170                 175

Met Asn Ala Leu Arg Val Ala Ser Asp Phe Val Arg Ala His Pro Asp
                180                 185                 190

Arg Lys Ser Leu Leu Val Cys Leu Glu Leu Ser Ser Val Asn Ala Val
                195                 200                 205

Phe Ala Gly Asp Pro Asn Asp Val Val Ile Ser Ser Leu Phe Ala Asp
                210                 215                 220

Gly Cys Gly Ala Ala Leu Ile Gly Ala Ser Glu Val Gly His Pro Leu
225                 230                 235                 240

Pro Ala Gly His Ile Val Val Arg Asp Thr Phe Ala His Leu Leu Asp
                245                 250                 255

Asp Ala Glu Asp Gly Ile Val Leu Gly Val Asn Ala Asn Gly Ile Thr
                260                 265                 270

Cys Glu Leu Ala His Ser Leu Pro Arg Tyr Ile Leu Asp Gly Val Ser
                275                 280                 285

Pro Val Ile Asp Gly Val Leu Ala Arg Asn Gly Leu Gly Arg Glu Asp
                290                 295                 300

Val Ala His Trp Ala Ile His Pro Gly Gly Pro Lys Ile Ile Glu Ser
305                 310                 315                 320

Ala Ser Ala Ala Leu Gly Leu Pro Arg Ser Ala Ser Gln Thr Ser Trp
                325                 330                 335

Ala Val Leu Ala Glu His Gly Asn Met Leu Ser Val Ser Leu Leu Phe
                340                 345                 350

Val Leu Glu Arg Leu Leu Gly Ala Arg Ala Ala Gly Gly Thr Gln Glu
                355                 360                 365

Thr Gly Leu Ala Phe Ser Phe Ala Pro Gly Val Thr Val Glu Gly Phe
                370                 375                 380

Leu Phe Asp Val Val Gly Gly Pro Ser
385                 390

<210> SEQ ID NO 2
<211> LENGTH: 412
<212> TYPE: PRT
<213> ORGANISM: Tsukamurella tyrosinosolvens

<400> SEQUENCE: 2

Met Thr Met Asn Ala Gly Ser Gln Gly Ala Pro Ala Leu Asp Val Pro
 1               5                  10                  15
```

Ala Pro Val Leu Pro Ala Pro Gly Thr Trp Leu Gly Ala Pro Pro Ala
            20                  25                  30

Pro Pro Thr Ser Val Ala Val Ile Glu Ser Leu Ala Thr Gly Ser Pro
        35                  40                  45

Ala Gln Thr Tyr Gly Gln Ala Glu Ser Ala Asp Arg Val Ala Ala Arg
    50                  55                  60

Phe Asp Asp Pro Arg Gln Ala Glu Arg Ile Arg Arg Val Tyr Ala Lys
65                  70                  75                  80

Thr Arg Val Asp Glu Arg His Leu Ala Ile Asp Pro Leu Thr Pro Glu
                85                  90                  95

Phe Ala Glu Phe Ser Thr Arg Pro Asp Thr Val Arg Gly Arg Met Asp
            100                 105                 110

Leu Phe Tyr Glu His Ala Ala Pro Leu Ala Val Asp Thr Ala Arg Arg
        115                 120                 125

Ala Leu Gly Val Gly Thr Glu His Glu Phe Asp Pro Ala Asp Val Gly
    130                 135                 140

Gln Leu Val Phe Val Thr Ser Thr Gly Phe Leu Ala Pro Gly Val Asp
145                 150                 155                 160

Val Ala Val Ile Arg Ala Leu Gly Leu Ala Pro Gln Thr Ser Arg Val
                165                 170                 175

Val Ile Asn Phe Met Gly Cys Ala Ala Ala Met Asn Ala Leu Arg Val
            180                 185                 190

Ser Thr Asp Tyr Val Arg Ala His Pro Asp Arg Lys Ser Leu Met Ile
        195                 200                 205

Cys Leu Glu Leu Ser Ser Val Asn Ala Val Phe Ser Gly Asp Pro Asn
    210                 215                 220

Asp Val Val Ile Ser Ser Leu Phe Ala Asp Gly Cys Gly Ala Ala Val
225                 230                 235                 240

Ile Gly Ala Ser Glu Val Gly His Pro Leu Pro Gly Gly Arg Ile Val
                245                 250                 255

Val Arg Asp Thr Phe Thr His Leu Leu Asp Gly Ala Glu Asp Gly Ile
            260                 265                 270

Val Leu Gly Val Asn Ala Asn Gly Ile Thr Cys Glu Leu Ala Glu Ser
        275                 280                 285

Leu Pro Gln Tyr Ile Val Asp Gly Val Ala Pro Val Ile Asp Glu Val
    290                 295                 300

Leu Gly Arg Asn Asp Leu Gly Arg Glu Ala Val Ala His Trp Ala Ile
305                 310                 315                 320

His Pro Gly Gly Pro Lys Ile Ile Glu Ser Ala Ala Thr Ala Leu Gly
                325                 330                 335

Leu Pro Asp Glu Ala Ser Arg Thr Ser Trp Asp Val Leu Ala Glu His
            340                 345                 350

Gly Asn Met Leu Ser Val Ser Leu Leu Phe Val Leu Glu Arg Leu Leu
        355                 360                 365

Ala Gln Val Ala Asp Gly Ala Thr Gln Pro Asp Gly Ala Pro Thr
    370                 375                 380

Thr Gly Met Ala Phe Ser Phe Ala Pro Gly Val Thr Val Glu Gly Phe
385                 390                 395                 400

Leu Phe Asp Val Val Thr Gly Asp Gln Pro Gly Glu
                405                 410

<210> SEQ ID NO 3
<211> LENGTH: 387
<212> TYPE: PRT

<213> ORGANISM: Tsukamurella pseudospumae

<400> SEQUENCE: 3

Met Ala Ala Pro Glu Leu Pro Gly Thr Ser Val Trp Arg Gly Ala Pro
1               5                   10                  15

Pro Ala Pro Pro Thr Ser Val Ala Val Ile Glu Ser Leu Ala Thr Gly
            20                  25                  30

Ser Pro Ser Gln Ala Tyr Asp Gln Ala Glu Ser Ala Asp Arg Val Ala
        35                  40                  45

Ser Arg Phe Asp Asp Pro Arg Gln Ala Glu Arg Ile Arg Arg Val Tyr
    50                  55                  60

Ala Lys Thr Arg Val Ala Glu Arg His Leu Ala Ile Asp Pro Leu Thr
65                  70                  75                  80

Pro Glu Phe Ala Ala Phe Ser Thr Arg Pro Asp Thr Ile Arg Glu Arg
                85                  90                  95

Met Asp Leu Phe Phe Glu His Ala Ala Pro Leu Ala Ile Asp Thr Ala
            100                 105                 110

Arg Arg Ala Leu Gly Thr Val Asp Pro Ala Asp Val Gly Gln Leu Val
            115                 120                 125

Phe Val Thr Ser Thr Gly Phe Leu Ala Pro Gly Val Asp Val Ala Val
130                 135                 140

Ile Arg Ala Leu Gly Leu Ser Pro Gly Thr Ser Arg Val Val Ile Asn
145                 150                 155                 160

Phe Met Gly Cys Ala Ala Ala Met Asn Ala Leu Arg Val Ser Thr Asp
                165                 170                 175

Tyr Val Arg Ala His Pro Asp Arg Lys Ser Leu Met Ile Cys Leu Glu
            180                 185                 190

Leu Ser Ser Val Asn Ala Val Phe Ser Gly Asp Pro Asn Asp Val Val
            195                 200                 205

Ile Ser Ser Leu Phe Ala Asp Gly Cys Gly Ala Ala Leu Ile Gly Ala
210                 215                 220

Ser Glu Val Gly His Pro Leu Pro Ala Gly Asn Ile Val Val Arg Asp
225                 230                 235                 240

Thr Phe Ser His Leu Leu Asp Gly Ala Glu Asp Gly Ile Val Leu Gly
                245                 250                 255

Val Asn Ala Asp Gly Ile Thr Cys Glu Leu Ala Glu Ser Leu Pro Gln
            260                 265                 270

Tyr Ile Val Asp Gly Val Ala Pro Val Val Asp Gly Val Leu Arg Arg
            275                 280                 285

Asn Gly Leu Asp Arg Asp Ala Val Ala His Trp Ala Ile His Pro Gly
290                 295                 300

Gly Pro Lys Ile Ile Glu Ser Ala Ser Thr Ala Leu Gly Leu Pro Asp
305                 310                 315                 320

Glu Ala Ser Arg Leu Ser Trp Asp Val Leu Ala Gly His Gly Asn Met
                325                 330                 335

Leu Ser Val Ser Leu Leu Phe Val Leu Glu Arg Leu Leu Ala Gln Val
            340                 345                 350

Ala Ser Asp Gly Ala Asp Gly Ala Pro Ser Thr Gly Met Ala Phe Ser
            355                 360                 365

Phe Ala Pro Gly Val Thr Val Glu Gly Phe Leu Phe Asp Val Val Thr
370                 375                 380

Thr Gly Glu
385

<210> SEQ ID NO 4
<211> LENGTH: 390
<212> TYPE: PRT
<213> ORGANISM: Tsukamurella pulmonis

<400> SEQUENCE: 4

Met Asn Thr Thr Glu Gln Gln Ser Val Leu Pro Gln Gln Ala Trp Leu
1               5                   10                  15

Gly Ala Pro Pro Ala Pro Pro Thr Ser Val Ala Val Ile Glu Ser Leu
            20                  25                  30

Ala Thr Ser Ser Pro Thr Gln Thr Tyr Gly Gln Ala Glu Ser Ala Asp
        35                  40                  45

Arg Val Ala Ala Arg Phe Asp Asp Pro Arg Gln Ala Glu Arg Ile Arg
    50                  55                  60

Arg Val Tyr Ala Lys Thr Arg Val Thr Glu Arg His Leu Ala Ile Asp
65                  70                  75                  80

Pro Leu Thr Pro Glu Phe Ala Glu Phe Ser Ala Arg Pro Asp Thr Val
                85                  90                  95

Arg Glu Arg Met Asp Leu Phe Phe Glu His Ala Ala Pro Leu Ala Ile
            100                 105                 110

Glu Thr Ala Arg Arg Ala Leu Gly Asp Asn Ala Ala Thr Asp Ile Gly
        115                 120                 125

Gln Leu Val Phe Val Thr Ser Thr Gly Phe Leu Ala Pro Gly Val Asp
    130                 135                 140

Val Ala Val Ile Arg Ala Leu Gly Leu Ala Pro Gln Thr Ser Arg Val
145                 150                 155                 160

Val Ile Asn Phe Met Gly Cys Ala Ala Ala Met Asn Ala Leu Arg Val
                165                 170                 175

Ser Thr Asp Tyr Val Arg Ala Gln Pro Asp Arg Lys Ser Leu Met Ile
            180                 185                 190

Cys Leu Glu Leu Ser Ser Val Asn Ala Val Phe Ser Gly Asp Pro Asn
        195                 200                 205

Asp Val Val Ile Ser Ser Leu Phe Ala Asp Gly Cys Gly Ala Ala Val
    210                 215                 220

Ile Gly Ala Ser Glu Val Gly His Pro Leu Pro Ser Gly Gln Ile Val
225                 230                 235                 240

Val Arg Asp Thr Phe Thr His Leu Leu Asp Gly Ala Glu Asp Gly Ile
                245                 250                 255

Val Leu Gly Val Asn Ala Asn Gly Ile Thr Cys Glu Leu Ala Glu Ser
            260                 265                 270

Leu Pro Gln Tyr Ile Val Asn Gly Val Ala Pro Val Val Asp Ala Val
        275                 280                 285

Leu Asp Arg Asn Gly Leu Gly Arg Glu Ala Val His Trp Ala Ile
    290                 295                 300

His Pro Gly Gly Pro Lys Ile Ile Glu Ser Ala Ala Ala Leu Gly
305                 310                 315                 320

Leu Pro Asp Asp Ala Ser Arg Leu Ser Trp Asp Val Leu Ala Glu His
                325                 330                 335

Gly Asn Met Leu Ser Val Ser Leu Leu Phe Val Leu Glu Arg Leu Arg
            340                 345                 350

Ala Gln Val Ala Ser Asp Gly Ala Asp Gly Ala Pro Ser Thr Gly Met
        355                 360                 365

Ala Phe Ser Phe Ala Pro Gly Val Thr Val Glu Gly Phe Leu Phe Asp
    370                 375                 380

Val Val Thr Thr Gly Glu
385                 390

<210> SEQ ID NO 5
<211> LENGTH: 397
<212> TYPE: PRT
<213> ORGANISM: Tsukamurella sp. 1534

<400> SEQUENCE: 5

Met Asn Ile Gln Asp Arg Ser Thr Val Ala Pro Asp Ser Pro Ala Leu
1               5                   10                  15

Gly Phe Pro Pro Ala Pro Pro Thr Ser Val Ala Val Ile Glu Ser Leu
            20                  25                  30

Ala Thr Gly Ser Pro Ser Gly Val His Ala Gln Ala Glu Ser Ala Asp
        35                  40                  45

Arg Val Ala Ser Arg Phe Asp Asp Pro Ala Gln Ala Glu Arg Ile Arg
    50                  55                  60

Arg Val Tyr Thr Lys Thr Arg Val Ala Arg His Leu Ala Ile Asp
65                  70                  75                  80

Pro Leu Asp Glu Asp Phe Ala Ala Phe Ser Ala Arg Pro Asp Thr Ile
                85                  90                  95

Arg Glu Arg Met Asp Leu Phe Ala Glu His Ala Ser Pro Leu Ala Val
            100                 105                 110

Asp Thr Ala Arg Arg Ala Leu Gly Ala Val Asp Pro Ala Asp Val Gly
        115                 120                 125

Gln Leu Val Phe Val Thr Ser Thr Gly Phe Leu Ala Pro Gly Val Asp
    130                 135                 140

Val Ala Ile Val Arg Ala Leu Gly Leu Pro Ala Thr Thr Ser Arg Val
145                 150                 155                 160

Ile Val Asn Phe Met Gly Cys Ala Ala Ala Met Asn Ala Leu Arg Val
                165                 170                 175

Ala Ser Asp Phe Val Arg Ala His Pro Asp Arg Lys Ser Leu Met Val
            180                 185                 190

Cys Leu Glu Leu Ser Ser Val Asn Ala Val Phe Ser Gly Asp Pro Asn
        195                 200                 205

Asp Val Val Ile Ser Ser Leu Phe Ala Asp Gly Cys Gly Ala Ala Val
    210                 215                 220

Ile Gly Ala Ser Glu Val Gly His Pro Leu Pro Gly Gly Ser Ile Val
225                 230                 235                 240

Val Arg Asp Thr Phe Ala His Leu Leu Asp Gly Ala Glu Asp Gly Ile
                245                 250                 255

Val Leu Gly Val Asn Ala Asn Gly Ile Thr Cys Glu Leu Ala Glu Ser
            260                 265                 270

Leu Pro Arg Tyr Ile Val Asp Gly Val Arg Pro Val Ile Asp Gly Val
        275                 280                 285

Leu Ala Arg Asn Gly Leu Gly His Ala Asp Val Ala His Trp Ala Ile
    290                 295                 300

His Pro Gly Gly Pro Lys Ile Ile Glu Ser Ala Ser Ala Ala Leu Gly
305                 310                 315                 320

Leu Pro Ala Ala Ala Ser Ala Thr Ser Trp Gln Val Leu Ala Glu His
                325                 330                 335

Gly Asn Met Leu Ser Val Ser Leu Leu Phe Val Leu Glu Arg Met Leu
            340                 345                 350

Ser Gly Leu Pro Asp Gly Ala Pro Ser Thr Gly Met Ala Phe Ser Phe

```
                355                 360                 365
Ala Pro Gly Val Thr Val Glu Gly Phe Leu Phe Asp Ile Val Arg Asp
    370                 375                 380

Gly Ala Pro Arg Pro Gly Ala Leu Gly Gly Arg Pro Ala
385                 390                 395

<210> SEQ ID NO 6
<211> LENGTH: 400
<212> TYPE: PRT
<213> ORGANISM: Nocardia farcinica

<400> SEQUENCE: 6

Met Ser Ile Thr Val Asp Glu Gly Gly Ala Arg Pro Ala Thr Glu Pro
1               5                   10                  15

Arg Gln Arg Ile His Pro Asp Leu Gly His Ala His Thr Pro Met Pro
            20                  25                  30

Pro Ala Pro Pro Val Thr Ile Gly Val Val Glu Gly Ile Ala Thr Gly
        35                  40                  45

Ser Pro Ala Gln Ile Val Asp Gln Ala Glu Ala Ala Glu Arg Val Ala
    50                  55                  60

Ala Leu Phe Thr Asp Pro Ala Gln Arg Ala Arg Ile Ala Arg Val Tyr
65                  70                  75                  80

Glu Lys Thr Arg Ile Glu Thr Arg Arg Met Ala Val Asp Pro Thr Ala
                85                  90                  95

Pro Glu Phe Arg Ser Phe Ser Arg Gln Pro Gly Thr Leu Arg Glu Arg
            100                 105                 110

Met Asn Leu Phe Tyr Arg His Ala Ala Pro Leu Ala Val Asp Val Ala
        115                 120                 125

Gly Arg Ala Leu Ala Asp Ser Gly Ala Ala Ala Asp Ile Gly Leu
    130                 135                 140

Leu Val Phe Val Thr Ser Thr Gly Phe Ile Ala Pro Gly Val Asp Val
145                 150                 155                 160

Ala Val Leu Arg Glu Leu Gly Leu Val Pro Thr Val Gly Arg Val Val
                165                 170                 175

Val Asn Phe Met Gly Cys Ala Ala Ala Met Asn Gly Ile Arg Thr Gly
            180                 185                 190

Val Asp Tyr Val Arg Ala His Pro Asp Lys Lys Ala Leu Val Val Cys
        195                 200                 205

Leu Glu Leu Ser Ser Val Asn Ala Val Phe Ala Asp Asp Val Asn Asp
    210                 215                 220

Val Ile Ile His Ser Leu Phe Gly Asp Gly Cys Gly Ala Val Val Leu
225                 230                 235                 240

Gly Ala Ser Gln Ala Arg Gln Pro Leu Ala Pro Gly Arg Val Val Val
                245                 250                 255

Arg Asp Ser Phe Ser His Leu Phe Asp Ala Ala Glu Asp Gly Ile Val
            260                 265                 270

Leu Gly Val Asp His Asn Gly Ile Thr Cys Glu Leu Ser Glu Asn Leu
        275                 280                 285

Pro Arg Tyr Ile Tyr Arg Gly Val Asp Pro Val Val Arg Glu Val Leu
    290                 295                 300

Ala Arg Asn Gly Leu Arg Lys Ser Asp Ile Asp Leu Trp Ala Ile His
305                 310                 315                 320

Pro Gly Gly Pro Lys Ile Ile Glu Glu Ser Val Arg Ser Leu Gly Leu
                325                 330                 335
```

-continued

```
Ser Pro Glu Gln Ala Ala Pro Ser Trp Asp Val Leu Ala Arg His Gly
                340                 345                 350

Asn Met Leu Ser Val Ser Leu Ile Phe Val Leu Glu Gln Met Ile Ala
            355                 360                 365

Gln Ser Ala Thr Ala Glu Pro Ile Ser Thr Gly Val Ala Phe Ser Phe
        370                 375                 380

Ala Pro Gly Val Thr Leu Glu Gly Leu Ile Phe Asp Ile Ile Arg Arg
385                 390                 395                 400

<210> SEQ ID NO 7
<211> LENGTH: 393
<212> TYPE: PRT
<213> ORGANISM: Mycobacterium marinum

<400> SEQUENCE: 7

Met Ser Thr Ala Ala Glu Gly Gly Ala Ile Arg Arg Ala Gly His Glu
1               5                   10                  15

Pro Arg Tyr Asp Leu Ala Gln Leu Pro Pro Ala Pro Thr Thr Val
            20                  25                  30

Ala Val Ile Glu Gly Met Ala Thr Gly Ala Pro Gln Arg Val Val Ala
            35                  40                  45

Gln Ala Asp Ala Ala Arg Val Ser Glu Leu Phe Val Asp Pro Gln
    50                  55                  60

Gln Arg Glu Arg Ile Ser Arg Ile Tyr Asp Lys Thr Arg Ile Asp Thr
65                  70                  75                  80

Arg Arg Met Ala Val Asp Pro Leu Asp Asp Glu Phe Asp Glu Phe Arg
                85                  90                  95

Arg Glu Pro Ala Thr Ile Arg Asp Arg Met Asn Leu Phe Tyr Gln His
            100                 105                 110

Ala Val Pro Leu Ala Val Asp Val Ala Ala Arg Ala Leu Asp Gly Leu
        115                 120                 125

Pro Tyr Ala Pro Asp Glu Ile Gly Gln Leu Val Phe Val Thr Ser Thr
130                 135                 140

Gly Phe Ile Ala Pro Gly Val Asp Val Glu Ile Val Lys Gln Leu Gly
145                 150                 155                 160

Leu Pro Arg Ser Ile Ser Arg Val Val Asn Phe Met Gly Cys Ala
            165                 170                 175

Ala Ala Met Asn Ala Ile Arg Thr Ala Thr Asn Tyr Val Arg Ala His
        180                 185                 190

Pro Ser Met Lys Ala Leu Val Val Cys Ile Glu Leu Ser Ser Val Asn
    195                 200                 205

Ala Val Phe Ala Asp Asp Ile Asn Asp Val Val Ile His Ser Leu Phe
210                 215                 220

Gly Asp Gly Cys Gly Ala Leu Val Ile Gly Ala Ser Gln Val Gln Gln
225                 230                 235                 240

Pro Leu Pro Ala Gly Asn Val Val Ile Arg Ser Ser Phe Ser Gln Leu
            245                 250                 255

Leu Asp Asp Ser Glu Asp Gly Ile Val Leu Gly Val Asn His Asp Gly
        260                 265                 270

Ile Thr Cys Glu Leu Ser Glu Asn Leu Pro Ser Tyr Ile Tyr Arg Ser
    275                 280                 285

Val Asp Pro Val Val Ala Glu Met Leu Arg Asn Gly Leu Ser Lys
290                 295                 300

Ala Asp Ile Asp Leu Trp Ala Ile His Pro Gly Gly Pro Lys Ile Ile
305                 310                 315                 320
```

```
Glu Gln Ser Ala Arg Ser Leu Gly Ile Pro Val Gly Arg Ala Val Gln
            325                 330                 335

Ser Trp Asp Val Leu Ala Gln Phe Gly Asn Met Leu Ser Val Ser Leu
            340                 345                 350

Ile Phe Val Leu Glu Met Met Val Ala Gln Ala Glu Ser Asp Lys Pro
            355                 360                 365

Ile Ser Thr Gly Val Ala Phe Ala Phe Ala Pro Gly Val Thr Val Glu
            370                 375                 380

Gly Met Leu Phe Asp Ile Ile Arg Arg
385                 390

<210> SEQ ID NO 8
<211> LENGTH: 395
<212> TYPE: PRT
<213> ORGANISM: Mycobacterium kansasii

<400> SEQUENCE: 8

Met Ser Ser Ala Ala Asp Gly Gly Ala Pro Val Ala Asp Val Pro Gly
1               5                   10                  15

Tyr Glu Pro His Tyr Asp Leu Ala Gln Leu Pro Pro Ala Pro Pro Thr
            20                  25                  30

Thr Val Ala Val Ile Glu Gly Met Ala Thr Gly Val Pro Gln Arg Val
            35                  40                  45

Val Arg Gln Ser Asp Ala Ala Arg Val Ala Gln Met Phe Val Asp
    50                  55                  60

Pro Gln Gln Arg Glu Arg Val Ser Arg Val Tyr Ala Lys Thr Arg Ile
65              70                  75                  80

Asp Thr Arg Arg Met Ala Val Asn Pro Leu Asp Ala Glu Phe Asp Ala
            85                  90                  95

Phe Arg Arg Glu Pro Ala Thr Ile Arg Asp Arg Met Ser Leu Phe Tyr
            100                 105                 110

Arg His Ala Val Pro Leu Ala Val Glu Val Thr Arg Arg Ala Leu Ala
            115                 120                 125

Gly Leu Ser Tyr Gly Ala Asp Glu Ile Gly Leu Leu Val Phe Val Thr
            130                 135                 140

Ser Thr Gly Phe Val Ala Pro Gly Val Asp Val Ala Ile Val Lys Glu
145             150                 155                 160

Leu Gly Leu Ser Arg Ala Ile Ser Arg Val Val Asn Phe Met Gly
            165                 170                 175

Cys Ala Ala Ala Met Asn Ala Ile Arg Thr Ala Thr Asn Tyr Val Arg
            180                 185                 190

Ala His Pro Ala Met Lys Ala Leu Val Val Cys Ile Glu Leu Cys Ser
            195                 200                 205

Val Asn Ala Val Phe Ala Asp Asn Val Lys Asp Val Ile His Ser
    210                 215                 220

Leu Phe Gly Asp Gly Cys Ala Ala Leu Val Ile Gly Ala Ser Gln Val
225                 230                 235                 240

Gln Gln Gln Leu Pro Ala Gly Ser Val Val Ile Arg Ser Asn Phe Ser
            245                 250                 255

Gln Leu Leu Asp Asp Ala Glu Asp Gly Ile Val Leu Gly Val Asn His
            260                 265                 270

Asp Gly Ile Thr Cys Glu Leu Ser Glu Asn Leu Pro Asp Tyr Ile Tyr
            275                 280                 285

Arg Gly Val Ala Pro Val Val Ala Asn Val Leu Tyr Asp Asn Gly Leu
```

```
                290                 295                 300

Gln Gln Ser Asp Ile Asp Leu Trp Ala Ile His Pro Gly Gly Pro Lys
305                 310                 315                 320

Ile Ile Glu Gln Ser Val Arg Ser Leu Gly Ile Gly Val Glu Cys Ala
                325                 330                 335

Ala Pro Ser Trp Asp Val Leu Ala Arg Tyr Gly Asn Met Leu Ser Val
                340                 345                 350

Ser Leu Ile Phe Val Leu Glu Met Met Val Gln Gln Ala Glu Ser Glu
                355                 360                 365

Lys Pro Leu Ser Thr Gly Val Ala Phe Ala Phe Ala Pro Gly Val Thr
            370                 375                 380

Val Glu Gly Met Leu Phe Asp Ile Val Arg Arg
385                 390                 395

<210> SEQ ID NO 9
<211> LENGTH: 334
<212> TYPE: PRT
<213> ORGANISM: Mycobacterium tuberculosis

<400> SEQUENCE: 9

Met Asn Val Ser Ala Glu Ser Gly Ala Pro Arg Arg Ala Gly Gln Arg
1               5                   10                  15

His Glu Val Gly Leu Ala Gln Leu Pro Pro Ala Pro Pro Thr Thr Val
                20                  25                  30

Ala Val Ile Glu Gly Leu Ala Thr Gly Thr Pro Arg Arg Val Val Asn
            35                  40                  45

Gln Ser Asp Ala Ala Asp Arg Val Ala Glu Leu Phe Leu Asp Pro Gly
        50                  55                  60

Gln Arg Glu Arg Ile Pro Arg Val Tyr Gln Lys Ser Arg Ile Thr Thr
65                  70                  75                  80

Arg Arg Met Ala Val Asp Pro Leu Asp Ala Lys Phe Asp Val Phe Arg
                85                  90                  95

Arg Glu Pro Ala Thr Ile Arg Asp Arg Met His Leu Phe Tyr Glu His
                100                 105                 110

Ala Val Pro Leu Ala Val Asp Val Ser Lys Arg Ala Leu Ala Gly Leu
            115                 120                 125

Pro Tyr Arg Ala Ala Glu Ile Gly Leu Leu Val Leu Ala Thr Ser Thr
        130                 135                 140

Gly Phe Ile Ala Pro Gly Val Asp Val Ala Ile Val Lys Glu Leu Gly
145                 150                 155                 160

Leu Ser Pro Ser Phe Gly Asp Gly Cys Ala Ala Leu Val Ile Gly Ala
                165                 170                 175

Ser Gln Val Gln Glu Lys Leu Glu Pro Gly Lys Val Val Arg Ser
            180                 185                 190

Ser Phe Ser Gln Leu Leu Asp Asn Thr Glu Asp Gly Ile Val Leu Gly
        195                 200                 205

Val Asn His Asn Gly Ile Thr Cys Glu Leu Ser Glu Asn Leu Pro Gly
        210                 215                 220

Tyr Ile Phe Ser Gly Val Ala Pro Val Val Thr Glu Met Leu Trp Asp
225                 230                 235                 240

Asn Gly Leu Gln Ile Ser Asp Ile Asp Leu Trp Ala Ile His Pro Gly
                245                 250                 255

Gly Pro Lys Ile Ile Glu Gln Ser Val Arg Ser Leu Gly Ile Ser Ala
                260                 265                 270
```

```
Glu Leu Ala Ala Gln Ser Trp Asp Val Leu Ala Arg Phe Gly Asn Met
            275                 280                 285

Leu Ser Val Ser Leu Ile Phe Val Leu Glu Thr Met Val Gln Gln Ala
            290                 295                 300

Glu Ser Ala Lys Ala Ile Ser Thr Gly Val Ala Phe Ala Phe Gly Pro
305                 310                 315                 320

Gly Val Thr Val Glu Gly Met Leu Phe Asp Ile Ile Arg Arg
                325                 330

<210> SEQ ID NO 10
<211> LENGTH: 370
<212> TYPE: PRT
<213> ORGANISM: Gordonia hydrophobica

<400> SEQUENCE: 10

Met Pro Ala Pro Val Thr Thr Val Ala Val Ile Glu Ala Val Ala Thr
1               5                   10                  15

Gly Ala Pro Ala Thr Val His Pro Gln Thr Arg Ala Ala Glu Gln Val
                20                  25                  30

Ala Glu Leu Tyr Asp Asp Pro Ala Leu Gln Glu Arg Ile Arg Arg Leu
            35                  40                  45

Tyr Arg Asn Thr Arg Val Gln Thr Arg His Leu Ala Val Asp Pro Met
50                  55                  60

Thr Pro Glu Phe Gln Glu Phe Ser Ser Arg Pro Ala Thr Val Arg Thr
65                  70                  75                  80

Arg Met Asn Asp Tyr Phe His His Ala Val Pro Leu Ala Val Asp Val
                85                  90                  95

Ala Arg Arg Ala Leu Ala Gly Val Thr Asp Pro Ala Thr Glu Ile Gly
            100                 105                 110

Gln Ile Ile Phe Val Thr Ser Thr Gly Phe Ile Ala Pro Gly Val Asp
            115                 120                 125

Val Ala Val Ile Thr Glu Leu Gly Leu Ala Pro Thr Val His Arg Val
130                 135                 140

Ile Ile Asn Phe Met Gly Cys Ala Ala Ala Ile Asn Gly Ile Ser Thr
145                 150                 155                 160

Ala Thr Asp His Val Arg Ala Asn Pro Asp Ser Arg Ala Leu Leu Ile
                165                 170                 175

Cys Leu Glu Leu Ser Ser Val Asn Ala Val Phe Gly Ala Asp Pro Val
            180                 185                 190

Glu Leu Val Thr His Ser Leu Phe Gly Asp Gly Cys Gly Ala Met Leu
            195                 200                 205

Ile Gly Ala Ser Pro Val Gly Arg Arg Leu Ala Pro Gly Gln Leu Val
        210                 215                 220

Val Arg Asp Thr Phe Ser His Leu Phe His Asp Thr Gly Asp Gly Ile
225                 230                 235                 240

Val Leu Gly Val Asn Asp Asp Gly Ile Thr Cys Glu Leu Ala Gln Glu
                245                 250                 255

Leu Pro Ser Tyr Ile Arg Arg Gly Val Gly Pro Ala Ile Asp Ala Ala
            260                 265                 270

Leu Asn Arg Ser Arg Leu Arg Arg Asp Asp Ile Ala His Trp Ala Ile
        275                 280                 285

His Pro Gly Gly Pro Ala Ile Ile Glu Gln Ser Val Ala Ala Leu Asp
        290                 295                 300

Leu Pro Pro Asp Arg Ala Ala Thr Ser Trp Glu Val Leu Ala Glu Tyr
305                 310                 315                 320
```

```
Gly Asn Met Leu Ser Val Ser Leu Val Phe Val Leu Glu Lys Leu Ile
                    325                 330                 335

Ala Ala Gly Ala His Gly Arg Gly Gln Ala Pro Glu Thr Gly Val Ala
                340                 345                 350

Phe Ser Phe Ala Pro Gly Val Ala Leu Glu Gly Met Leu Phe Asp Leu
            355                 360                 365

Val Cys
    370

<210> SEQ ID NO 11
<211> LENGTH: 349
<212> TYPE: PRT
<213> ORGANISM: Pseudomonas fluorescens Pf5

<400> SEQUENCE: 11

Met Ser Thr Leu Cys Leu Pro His Val Met Phe Pro Gln His Lys Ile
1               5                   10                  15

Thr Gln Gln Met Val Asp His Leu Glu Asn Leu His Ala Asp His
            20                  25                  30

Pro Arg Met Ala Leu Ala Lys Arg Met Ile Ala Asn Thr Glu Val Asn
        35                  40                  45

Glu Arg His Leu Val Leu Pro Ile Asp Glu Leu Ala Val His Thr Gly
    50                  55                  60

Phe Thr His Arg Ser Ile Val Tyr Glu Arg Glu Ala Arg Gln Met Ser
65                  70                  75                  80

Ser Ala Ala Ala Arg Gln Ala Ile Glu Asn Ala Gly Leu Gln Ile Ser
                85                  90                  95

Asp Ile Arg Met Val Ile Val Thr Ser Cys Thr Gly Phe Met Met Pro
            100                 105                 110

Ser Leu Thr Ala His Leu Ile Asn Asp Leu Ala Leu Pro Thr Ser Thr
        115                 120                 125

Val Gln Leu Pro Ile Ala Gln Leu Gly Cys Val Ala Gly Ala Ala Ala
    130                 135                 140

Ile Asn Arg Ala Asn Asp Phe Ala Arg Leu Asp Ala Arg Asn His Val
145                 150                 155                 160

Leu Ile Val Ser Leu Glu Phe Ser Ser Leu Cys Tyr Gln Pro Asp Asp
                165                 170                 175

Thr Lys Leu His Ala Phe Ile Ser Ala Ala Leu Phe Gly Asp Ala Val
            180                 185                 190

Ser Ala Cys Val Leu Arg Ala Asp Asp Gln Ala Gly Gly Phe Lys Ile
        195                 200                 205

Lys Lys Thr Glu Ser Tyr Phe Leu Pro Lys Ser Glu His Tyr Ile Lys
    210                 215                 220

Tyr Asp Val Lys Asp Thr Gly Phe His Phe Thr Leu Asp Lys Ala Val
225                 230                 235                 240

Met Asn Ser Ile Lys Asp Val Ala Pro Val Met Glu Arg Leu Asn Tyr
                245                 250                 255

Glu Ser Phe Glu Gln Asn Cys Ala His Asn Asp Phe Ile Phe His
            260                 265                 270

Thr Gly Gly Arg Lys Ile Leu Asp Glu Leu Val Met His Leu Asp Leu
        275                 280                 285

Ala Ser Asn Arg Val Ser Gln Ser Arg Ser Ser Leu Ser Glu Ala Gly
    290                 295                 300

Asn Ile Ala Ser Val Val Val Phe Asp Val Leu Lys Arg Gln Phe Asp
```

Ser Asn Leu Asn Arg Gly Asp Ile Gly Leu Leu Ala Ala Phe Gly Pro
305                 310                 315                 320

Gly Phe Thr Ala Glu Met Ala Val Gly Glu Trp Thr Ala
            340                 345

<210> SEQ ID NO 12
<211> LENGTH: 381
<212> TYPE: PRT
<213> ORGANISM: Ectocarpus siliculosus

<400> SEQUENCE: 12

Met Ser Lys Asp Glu Gln Thr Val Tyr Pro Val Ile Ala Gly Met Ala
1               5                   10                  15

Ile Gly Asn Pro Gln Tyr Arg Cys Thr Gln Asn Glu Ala Leu Ala Val
            20                  25                  30

Ala Ser Lys Cys Pro Gly Leu Glu Ser Ile Lys Pro Val Leu Glu Arg
        35                  40                  45

Ile Tyr Gly Asn Ser Arg Ile Gly Ser Arg Tyr Phe Ala Val Pro Asp
    50                  55                  60

Phe Thr Pro Gly Arg Ala Ala Lys Gly Asp Pro Leu Phe Tyr Pro Ala
65                  70                  75                  80

Asp Gly Ser Tyr Gln Val Pro Val Asp Val Arg Leu Asp Lys Phe Lys
                85                  90                  95

Glu Lys Ala Val Pro Leu Val Ser Asp Val Ala Arg Arg Ala Ile Lys
            100                 105                 110

Glu Ala Gly Leu Asn Val Glu Asp Ile Ser Lys Leu Val Val Val Ser
        115                 120                 125

Ser Thr Gly Phe Leu Gly Pro Gly Leu Asp Cys Glu Leu Ile Lys Asn
    130                 135                 140

Leu Gly Leu Thr Arg Ser Val Asp Arg Thr Leu Ile Gly Phe Met Gly
145                 150                 155                 160

Cys Ala Ala Ala Met Asn Gly Phe Arg Asn Ala Asn Asp Tyr Val Thr
                165                 170                 175

Ala Asn Pro Gly Lys Tyr Ala Leu Met Ile Cys Val Glu Leu Ser Ser
            180                 185                 190

Val His Thr Thr Phe Asp Asp Asn Ile Asn Asp Ala Ile Leu His Ala
        195                 200                 205

Ile Phe Ala Asp Gly Cys Ala Ala Val Leu Lys Gly Ala Arg Lys
    210                 215                 220

Ser Glu Cys Pro Lys Gly Thr Leu Ala Ile Val Asp Asn His Ala Trp
225                 230                 235                 240

Leu Met Glu Gly Thr Glu Asp Gly Ile Thr Leu Ala Ile Lys Pro Asn
                245                 250                 255

Gly Ile Thr Cys Thr Leu Ser Lys Phe Leu Pro Gln Tyr Ile Ala Lys
            260                 265                 270

Asn Ile Ala Phe Phe Ala Asp Gly Phe Leu Lys His Lys Leu Gly
        275                 280                 285

Arg Asp Asp Val Asp Phe Trp Cys Val His Pro Gly Gly Arg Arg Ile
    290                 295                 300

Ile Glu Glu Ala Gln Asn Gly Leu Gly Leu Ser Glu Glu Gln Thr Ala
305                 310                 315                 320

Asp Ser Trp Ala Val Leu Gly Glu Tyr Gly Asn Met Leu Ser Pro Ser
                325                 330                 335

Val Met Phe Val Leu Ser Arg Val Phe Lys Arg His Asn Ala Ala Leu
            340                 345                 350

Ala Gln Gly Lys Pro Gly Tyr Gln Thr Gly Met Ala Phe Ser Phe Ser
        355                 360                 365

Pro Gly Val Gly Ala Glu Gly Ile Leu Leu Arg Gln Ile
370                 375                 380

<210> SEQ ID NO 13
<211> LENGTH: 598
<212> TYPE: DNA
<213> ORGANISM: Saccharomyces cerevisiae

<400> SEQUENCE: 13
tatcttaact gatagtttga tcaaaggggc aaaacgtagg ggcaaacaaa cggaaaaatc      60
gtttctcaaa ttttctgatg ccaagaactc taaccagtct tatctaaaaa ttgccttatg     120
atccgtctct ccggttacag cctgtgtaac tgattaatcc tgcctttcta atcaccattc     180
taatgtttta attaagggat tttgtcttca ttaacggctt tcgctcataa aaatgttatg     240
acgttttgcc cgcaggcggg aaaccatcca cttcacgaga ctgatctcct ctgccggaac     300
accgggcatc tccaacttat aagttggaga ataagagaa tttcagattg agagaatgaa     360
aaaaaaaaaa aaaaaaggca gaggagagca tagaaatggg gttcactttt tggtaaagct     420
atagcatgcc tatacatat aaatagagtg ccagtagcga ctttttcac actcgaaata     480 ctcttactac tgctctcttg ttgtttttat cacttcttgt ttcttcttgg taaatagaat     540
atcaagctac aaaagcata caatcaacta tcaactatta actatatcgt aatacaca      598

<210> SEQ ID NO 14
<211> LENGTH: 998
<212> TYPE: DNA
<213> ORGANISM: Saccharomyces cerevisiae

<400> SEQUENCE: 14
aaccagggca agcaaaata aagaaactt aatacgttat gccgtaatga agggctacca       60
aaaacgataa tctcaactgt aaacaggtac aatgcggacc cttttgccac aaaacataca    120
tcattcattg ccggaaaaag aaagaagtga agacagcagt gcagccagcc atgttgcgcc    180
aatctaatta tagatgctgg tgccctgagg atgtatctgg agccagccat ggcatcatgc    240
gctaccgccg gatgtaaaat ccgacacgca aagaaaacc ttcgaggttg cgcacttcgc    300
ccacccatga ccacacggt tagtccaaaa ggggcagttc agattccaga tgcgggaatt    360
agcttgctgc caccctcacc tcactaacgc tgcggtgtgc ggatacttca tgctatttat    420
agacgcgcgt gtcggaatca gcacgcgcaa gaaccaaatg ggaaaatcgg aatgggtcca    480
gaactgcttt gagtgctggc tattggcgtc tgatttccgt tttgggaatc ctttgccgcg    540 cgccctctc aaaactccgc acaagtccca gaaagcggga agaaataaa acgccaccaa     600 aaaaaaaaat aaaagccaat cctcgaagcg tgggtggtag gccctggatt atcccgtaca    660
agtatttctc aggagtaaaa aaaccgttg ttttggaatt ccccatttcg cggccaccta    720
cgccgctatc tttgcaacaa ctatctgcga taactcagca aattttgcat attcgtgttg    780
cagtattgcg ataatgggag tcttacttcc aacataacgg cagaaagaaa tgtgagaaaa    840
ttttgcatcc tttgcctccg ttcaagtata taagtcggc atgcttgata atctttcttt    900
ccatcctaca ttgttctaat tattcttatt ctccttttatt ctttcctaac ataccaagaa   960
attaatcttc tgtcattcgc ttaaacacta tatcaata                            998

```
<210> SEQ ID NO 15
<211> LENGTH: 300
<212> TYPE: DNA
<213> ORGANISM: Saccharomyces cerevisiae

<400> SEQUENCE: 15
gaagttttgt tagaaaataa atcatttttt aattgagcat tcttattcct attttattta      60
aatagtttta tgtattgtta gctacataca acagtttaaa tcaaattttc tttttcccaa     120
gtccaaaatg gaggtttatt ttgatgaccc gcatgcgatt atgttttgaa agtataagac     180
tacatacatg tacatatatt taaacatgta aacccgtcca ttatattgct tactttcttc     240 tttttttgccg ttttgacttg gacctctggt ttgctatttc cttacaatct ttgctacaat    300
```

USE OF TYPE III POLYKETIDE SYNTHASES FROM BACTERIA AS PHLOROGLUCINOL SYNTHASES

FIELD OF THE INVENTION

The present invention lies in the fields of microbial biochemistry and more particularly in the field of the synthesis of phloroglucinol by microbial enzymes. It relates to the use of type III polyketide synthases from bacteria, in particular from actinomycete bacteria, as phloroglucinol synthases.

BACKGROUND

Phloroglucinol is an aromatic organic compound used in particular in the production of pharmaceutical products and explosives.

Phloroglucinol synthesis is catalysed by type III polyketide synthases known as phloroglucinol synthases. Phloroglucinol synthases carry out the condensation of three malonyl-CoA molecules so as to form a phloroglucinol molecule according to the following reaction scheme (Reaction I):

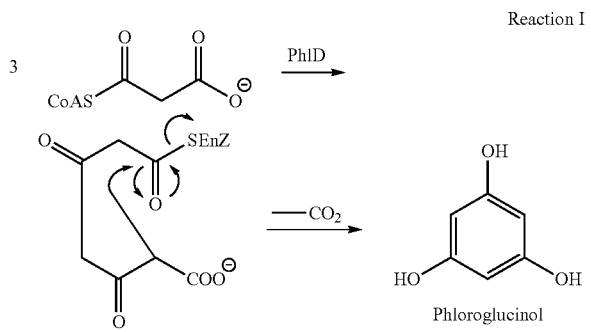

Numerous oligomers can subsequently be synthesized from phloroglucinol, such as phlorotannins. Phlorotannins include in particular fucols, phloretols and fucophloretols, which are phloroglucinol-derived products that make up the wall of brown algae. In addition, various protective activities of brown algae have also been attributed to phlorotannins.

At the current time, phloroglucinol synthesis has been described only in Gram– *Pseudomonas fluorescens* bacteria (Achkar et al., 2005; Zha et al., 2006) and in the brown alga *Ectocarpus siliculosus* (Meslet-Cladière et al., 2013). The phloroglucinol synthase enzyme involved in phloroglucinol synthesis has been identified in these two species. They are the only two phloroglucinol synthases identified and characterized to date.

In *Pseudomonas fluorescens*, the phloroglucinol synthase is encoded by the PHLD gene (Achkar et al., 2005; Zha et al., 2006).

In *Ectocarpus siliculosus*, the phloroglucinol synthase is encoded by the PKS1 gene (Meslet-Cladière et al., 2013).

It has been possible to demonstrate PHLD phloroglucinol synthase activity in *Escherichia coli* expressing a heterologous PHLD gene (Achkar et al., 2005). This activity has been confirmed in vitro, by means of small-scale enzymatic tests carried out with a recombinant PHLD expressed and purified from *Escherichia coli* cultures (Zha et al., 2006).

PKS1 phloroglucinol synthase activity has been demonstrated in vitro, from recombinant PKS1 expressed and purified in *Escherichia coli* and from cell extracts of *E. siliculosus* (Meslet-Cladière et al., 2013, WO 2013/045510).

However, the PHLD and PKS1 enzymes exhibit low enzymatic activities. In addition, the possibility of synthesizing phloroglucinol in vitro on a large scale using these enzymes has never been proved. Finally, the phloroglucinol synthases used in these studies were produced by *E. coli* or *P. fluorescens* bacteria. The activity of these enzymes when they are produced by eukaryotics, such as yeasts or insect or mammalian cells, is thus unknown. However, the eukaryotic systems may be advantageous, in particular for large-scale productions. They in fact make it possible to obtain enzymes which can be modified at the post-translational level.

Thus, there is still the need to identify new phloroglucinol synthases which have a high phloroglucinol synthesis enzymatic activity in vitro or in vivo, which are suitable for industrial-scale production and which can be produced by eukaryotic systems.

The exact functional characterization of a polyketide synthase is, however, complicated by the fact that this class of enzymes brings together proteins which have large sequence similarities, whereas they can catalyse substantially dissimilar reactions and recognize entirely different substrates.

Despite these difficulties, the present inventors have been able to identify polypeptides which are present in the bacteria and have phloroglucinol synthase activity. Thus, new phloroglucinol synthases have been identified, in particular in Gram+ bacteria. They constitute the first example of phloroglucinol synthases in bacteria of this type. The inventors demonstrate here that these new phloroglucinol synthases exhibit a high phloroglucinol synthesis activity. They are thus suitable for industrial-scale production. Furthermore, they are functional when they are produced in a eukaryotic system.

SUMMARY OF THE INVENTION

In the context of the present invention, the inventors have demonstrated, entirely surprisingly, that bacteria, in addition to *Pseudomonas fluorescens*, contain in their genome a gene encoding a type III polyketide synthase having a functional phloroglucinol synthase activity.

The present invention thus relates to polypeptides chosen from type III polyketide synthases from bacteria, in particular type III polyketide synthases from gram+ bacteria, in particular the type III polyketide synthases from actinomycete bacteria, which can be used as phloroglucinol synthases.

The present invention also relates to isolated nucleic acid molecules encoding phloroglucinol synthases from bacteria, in particular encoding phloroglucinol synthases from gram+ bacteria, in particular for type III polyketide synthases from actinomycete bacteria, and also to the phloroglucinol synthases thus encoded.

The invention also relates to vectors comprising at least one isolated nucleic acid molecule encoding such a phloroglucinol synthase.

The invention also relates to host cells comprising at least one isolated nucleic acid molecule or at least one vector according to the invention.

The invention also relates to methods for producing a functional phloroglucinol synthase.

The invention also relates to methods for producing phloroglucinol.

DESCRIPTION OF THE FIGURES

FIG. 3 shows an example of the structure of a gene unit constructed for a given candidate (PhlD.ii), making it possible to express the PHLD genes in the yeast *Saccharomyces cerevisiae*.

DETAILED DESCRIPTION OF THE INVENTION

Definitions

Figure 1:
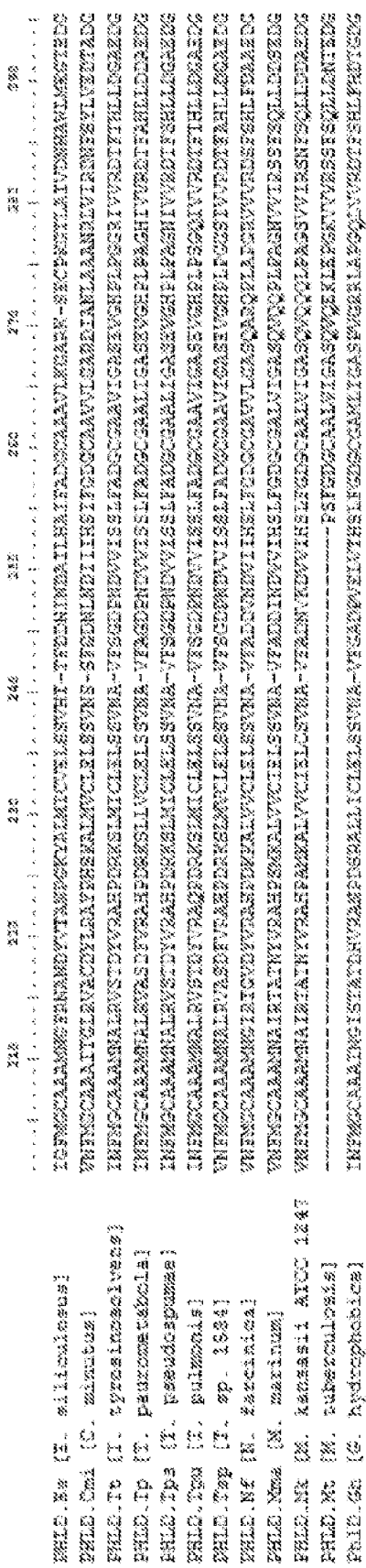
FIG. 1 presents the protein sequence alignment of the identified candidate enzymes. The alignment of the ten selected enzymes with the enzyme PKS1.Es (PHLD.Es) was carried out using the Clustal W software.
Figure 1:
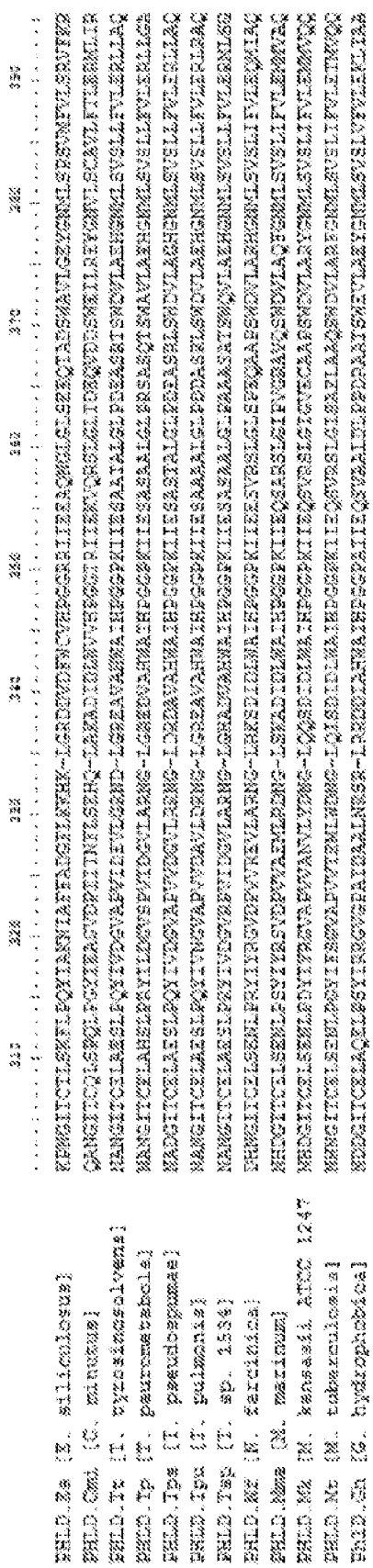
Figure 1:
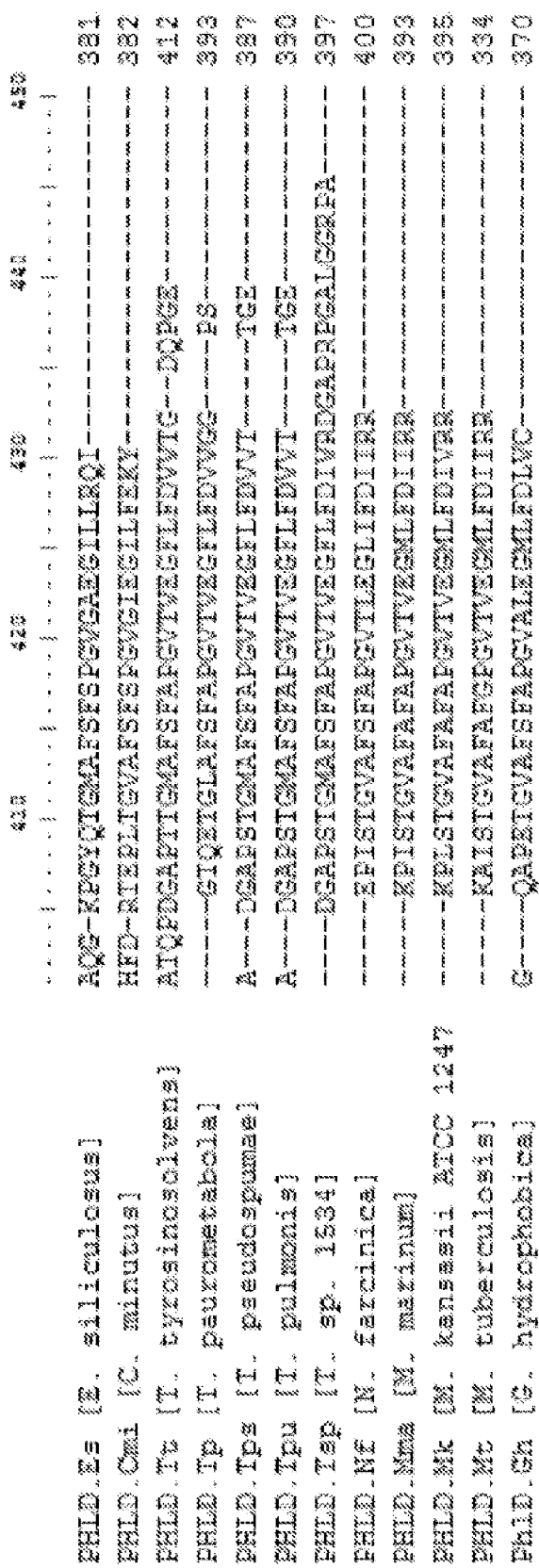

The term "type III polyketide synthase" is intended to mean a multifunctional enzyme or an enzymatic complex producing polyketides and which does not use an acyl carrier protein (or ACP) domain.

The term "polyketide" is intended to mean a large family of secondary metabolites in bacteria, mycetes, plants and certain animal lines which originate from the iterative condensation of acetyl or malonyl subunits by polyketide-synthase enzymes. Polyketides also serve as starting materials for the production of a wide range of natural and semi-synthetic products.

The term "phloroglucinol" is intended to mean an aromatic organic compound benzene-1,3,5-triol having the following chemical formula (formula I):

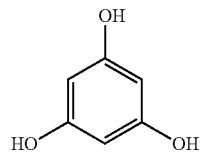

Formula I

The term "phloroglucinol synthase" is intended to mean a multifunctional enzyme or an enzymatic complex which belongs to the family of type III polyketide synthases and which catalyses phloroglucinol synthesis. A phloroglucinol synthase catalyses the condensation of three malonyl-CoA molecules so as to form a phloroglucinol molecule.

The term "enzymatic activity" or "catalytic activity" or else "activity" of an enzyme is intended to mean the efficiency of an enzyme to convert a substrate into a product in a given environment. The efficiency of the enzyme takes into account here the rate of conversion of the substrate into a product by the enzyme and the degree of conversion of the substrate into a product by the enzyme. The expression "degree of conversion of the substrate into a product by the enzyme" is intended to mean here the ratio between the amount of final product obtained relative to the initial amount of substrate for a defined amount of enzyme. For example, for the purposes of the invention, an enzymatic activity can be expressed as an amount of phloroglucinol produced in a given volume (in g/l).

The term "bacterium" is intended to mean a microscopic and prokaryotic organism present in all media.

The term "Gram+ bacterium" or "Gram-positive bacterium" is intended to mean a bacterium which is positive upon Gram staining (that is to say which retains the gentian violet, also known as crystal violet, and remains mauve-violet-coloured or blue-dark purple-coloured).

The term "actinomycete bacterium" or "Gram+ actinomycete bacterium" or "Gram-positive actinomycete bacterium" is intended to mean a bacterium belonging to the order Actinomycetales in the classification of actinobacteria, which is positive with respect to Gram staining. Actinomycetes are bacteria, the growth of which give rise to colonies consisting of hyphae, that is to say filaments which radiate, by centrifugal growth, all around the microorganism which gave rise to them.

The term "*Tsukamurella* sp." is intended to mean a rod-shaped, necessarily aerobic, non-sporulating actinomycete bacterium of the *Tsukamurella* genus. The *Tsukamurella* genus comprises in particular the species *Tsukamurella paurometabola* (also referred to as Tp hereinafter), *Tsukamurella tyrosinosolvens* (also referred to as Tt hereinafter), *Tsukamurella pseudospumae* (also referred to as Tps hereinafter), *Tsukamurella pulmonis* (also referred to as Tpu hereinafter) and *Tsukamurella* sp. 1534 (also referred to as Tsp hereinafter).

The term "*Nocardia* sp." is intended to mean a filamentous actinomycete bacterium of the *Nocardia* genus. The *Nocardia* genus comprises in particular the species *Nocardia farcinica* (also referred to as Nf hereinafter).

The term "*Mycobacterium* sp." is intended to mean a non-sporulating, aerobic actinomycete bacterium, in the shape of bacilli, of the *Mycobacterium* genus. The *Mycobacterium* genus comprises in particular the species *Mycobacterium marinum*, *Mycobacterium kansasii* and *Mycobacterium tuberculosis* (also respectively referred to as Mma, Mk and Mt hereinafter).

The term "*Gordonia* sp." is intended to mean an actinomycete bacterium of the *Gordonia* genus. The *Gordonia* genus comprises in particular the species *Gordonia hydrophobica* (also referred to as Gh hereinafter).

The term "*Pseudomonas* sp." is intended to mean a Gram-negative (Gram−) bacterium, which does not form spores (or non-sporulating), which is in the form of a *bacillus* and which is necessarily aerobic, of the *Pseudomonas* genus. The *Pseudomonas* genus comprises in particular the species *Pseudomonas fluorescens* (also known as Pf hereinafter).

The term "*Ectocarpus* sp." is intended to mean an alga of the *Ectocarpus* genus, of the class of brown algae, belonging to the family Ectocarpaceae. The *Ectocarpus* genus comprises in particular the species *Ectocarpus siliculosus*.

The term "PHLD.Pf" is intended to mean, without distinction, the gene encoding the PHLD phloroglucinol synthase of *P. fluorescens*, or the polypeptide encoded by this gene.

The term "PKS1.Es" or "PHLD.Es" is intended to mean, without distinction, the gene encoding the PKS1 phloroglucinol synthase of *E. siliculosus*, or the polypeptide encoded by this gene.

The term "PhID" or "PHLD" denotes here a candidate gene encoding a candidate phloroglucinol synthase enzyme, or the polypeptide encoded by this gene. According to the nomenclature chosen by the inventors, the term "PhID.ii" or "PHLD.ii" denotes here the candidate gene or the candidate polypeptide from a given organism. The letters "ii" represent the genus and the species to which said organism belongs.

The term "nucleic acid molecule" is intended to mean a polymer of any length of deoxyribonucleic acid (DNA), or polydeoxyribonucleotides, including in particular complementary DNAs or cDNAs, genomic DNAs, plasmids, vectors, viral genomes, isolated DNA, probes, primers and any mixture thereof; or a polymer of any length of ribonucleic acid (RNA), or polyribonucleotides, including in particular messenger RNAs or mRNAs, antisense RNAs; or mixed polyribo-polydeoxyribonucleotides. They encompass single-stranded or double-stranded, linear or circular, and natural or synthetic polynucleotides. In addition, a polynucleotide can comprise non-natural nucleotides and can be interrupted by non-nucleotide components. In the context of the present invention, the terms "nucleic acid", "nucleic acid molecule", "polynucleotide" and "nucleotide sequence" are used interchangeably.

The term "isolated molecule" is intended to mean a molecule, in particular a protein, a polypeptide, a peptide, a nucleic acid molecule, a plasmid vector, a viral vector or a host cell, which is extracted from its natural environment (that is to say separated from at least one other component with which it is naturally associated).

The term "polypeptide", "protein" and "peptide" is intended to mean polymers of amino acid residues which comprise at least nine amino acids bonded via peptide bonds. The polymer may be linear, branched or cyclic. The polymer may comprise natural amino acids and/or amino acid analogues and it may be interrupted by non-amino acid residues. As a general indication and without however being bound thereto in the present application, if the amino acid polymer contains more than 50 amino acid residues, it is preferably referred to as a polypeptide or a protein, whereas if the polymer consists of 50 amino acids or less, it is preferably referred to as a "peptide".

The term "vector" is intended to mean a carrier, preferably a nucleic acid molecule or a viral particle, which contains the elements required to enable one or more nucleic acid molecule(s) to be administered into, propagated in and/or expressed in a host cell or an organism.

From a functional point of view, this term encompasses maintenance vectors (cloning vectors), vectors for expression in various host cells or organisms (expression vectors), extrachromosomal vectors (for example multicopy plasmids) or integrating vectors (for example designed to integrate into the genome of a host cell and to produce additional copies of the nucleic acid molecule that it contains when the host cell replicates). This term also encompasses shuttle vectors (for example, which function both in prokaryotic hosts and/or eukaryotic hosts) and transfer vectors (for example for the transfer of nucleic acid molecule(s) into the genome of a host cell).

From a structural point of view, the vectors according to the invention may be natural, synthetic or artificial genetic sources, or a combination of natural and artificial genetic elements.

Thus, in the context of the invention, the term "vector" should be understood broadly while including plasmid vectors (or plasmids) and viral vectors.

A "plasmid" as used here denotes a replicatable DNA construct. Usually, plasmid vectors contain selectable marker genes which allow the host cells carrying the plasmid to be identified and/or selected positively or negatively in the presence of the compound corresponding to the selectable marker. A variety of positive and negative selectable marker genes are known in the art. By way of illustration, an antibiotic resistance gene can be used as a positive selectable marker gene for selecting a host cell in the presence of the corresponding antibiotic.

The term "viral vector" as used here refers to a nucleic acid vector which comprises at least one element of a viral genome and which can be packaged in a viral particle, or a viral particle. The viral vectors may be replication-competent or selective (for example, designed to replicate better or selectively in specific host cells), or may be genetically deactivated so as to be defective or deficient for replication.

The term "host cell" is intended to mean a cell containing a nucleic acid molecule according to the invention. Advantageously, the host cell is capable of expressing a polypeptide with phloroglucinol synthase activity and/or of producing the vector of the invention. Advantageously again, the host cell is capable of synthesizing phloroglucinol.

The host cell may consist of a single type of cells or of a group of different types of cells. The host cell may also be a hybrid cell, that is to say a cell resulting from the fusion of at least two cells of different type.

The host cell may belong to cultured cell lines, to primary cells, to stem cells or to proliferative cells. In the context of the invention, the term "host cells" comprises prokaryotic cells, lower eukaryotic cells such as yeast cells, and other eukaryotic cells such as insect cells, plant cells and mammalian cells (for example human or nonhuman cells, preferably nonhuman cells).

The term "host cell" comprises more broadly cells which contain or have contained the nucleic acid molecule according to the invention, and also the progeny of such cells. The host cell may for example be isolated or organized in a tissue or in an organ or else may be within a complete organism. In the case where the host cell is within a complete organism, said organism is not human.

It is thus clear that a "host cell" according to the present invention is a recombinant host cell, i.e. a cell housing an exogenous genetic material. Thus, a host cell is not a cell that exists naturally, but is a molecular biology tool obtained by genetic manipulation techniques.

The term "identity" is intended to mean an exact sequence correspondence between two polypeptides or two amino acid molecules. The "percentage identity" between two sequences depends on the number of identical residues common to the two sequences, and takes into account the number of intervals that must be introduced for an optimal alignment and the length of each interval. Various computer programs and mathematical algorithms are available in the prior art for determining the percentage identity between amino acid sequences, such as for example the Blast program available on the NCBI or ALIGN base (Atlas of Protein Sequence and Structure, Dayhoff (ed.), 1981, Suppl. 3 482-489). Programs for determining the homology between nucleotide sequences are also available in a specialized database (for example Genbank, the Wisconsin Sequence Analysis Package, the BESTFIT, FASTA and GAP programs). By way of illustration, the expression "at least 80% sequence identity", as used here, represents 80%, 81%, 82%, 83%, 84%, 85%, 86%, 87%, 88%, 89%, 90%, 91%, 92%, 93%, 94%, 95%, 96%, 97%, 98%, 99% or 100%.

In the detailed description which follows, the embodiments may be taken alone or combined appropriately by those skilled in the art.

Isolated Polypeptides and Use Thereof as Phloroglucinol Synthases

The focus herein is on the isolated polypeptides chosen from type III polyketide synthases of bacteria, in particular from type III polyketide synthases of gram+ bacteria, in particular from type III polyketide synthases of actinomycete bacteria.

In point of fact, the inventors have identified, entirely surprisingly, genes encoding new type III polyketide synthases in the genome of bacteria that was not known to encode this type of enzyme. The inventors have in particular demonstrated, most surprisingly, that these novel type III polyketide synthases have phloroglucinol synthase activity.

The present invention relates in particular to the use of isolated polypeptides chosen from type III polyketide synthases of bacteria as phloroglucinol synthases, preferably with the exclusion of the type III polyketide synthase of *Pseudomonas fluorescens* PHLD.Pf. The present invention relates in particular to the use of isolated polypeptides chosen from type III polyketide synthases of bacteria as phloroglucinol synthases, with the exclusion of the type III polyketide synthase of *Pseudomonas fluorescens* PHLD.Pf.

The present invention also relates in particular to the use of isolated polypeptides chosen from the type III polyketide synthases of gram+ bacteria, in particular from the type III polyketide synthases of actinomycete bacteria, as phloroglucinol synthases.

Advantageously, said polypeptide comprises at least one amino acid sequence having at least 50% identity with a sequence chosen from SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9 and SEQ ID No. 10.

Advantageously, said isolated polypeptide is chosen from the type III polyketide synthases of gram+ bacteria. Advantageously, said isolated polypeptide is chosen from the type III polyketide synthases of actinomycete bacteria chosen from the group consisting of *Tsukamurella* sp., *Nocardia* sp., *Mycobacterium* sp., and *Gordonia* sp., in particular *Tsukamurella paurometabola*, *Tsukamurella tyrosinosolvens*, *Tsukamurella pseudospumae*, *Tsukamurella pulmonis*, *Tsukamurella* sp. 1534, *Nocardia farcinica*, *Mycobacterium marinum*, *Mycobacterium kansasii*, *Mycobacterium tuberculosis* and *Gordonia hydrophobica*.

According to one embodiment, said polypeptide comprises at least one amino acid sequence preferably having at least 60% identity, more preferably at least 65% identity, more preferably at least 70% identity, even more preferably at least 75% identity, still more preferably at least 80% identity, even more preferentially at least 85% identity, even more preferentially at least 90% identity, more preferably at least 95% identity, more preferably at least 96% identity, even more preferably at least 97% identity, still more preferably at least 98% identity, and even more preferentially at least 99% identity, with a sequence chosen from SEQ ID No.: 1, SEQ ID No.: 2, SEQ ID No.: 3, SEQ ID No.: 4, SEQ ID No.: 5, SEQ ID No.: 6, SEQ ID No.: 7, SEQ ID No.: 8, SEQ ID No.: 9 and SEQ ID No.: 10.

According to one particularly advantageous embodiment, said polypeptide comprises at least one amino acid sequence chosen from SEQ ID No.: 1 SEQ ID No.: 2, SEQ ID No.: 3, SEQ ID No.: 4, SEQ ID No.: 5, SEQ ID No.: 6, SEQ ID No.: 7, SEQ ID No.: 8, SEQ ID No.: 9 and SEQ ID No.: 10.

In one preferred embodiment, the isolated polypeptide with phloroglucinol synthase activity has an amino acid sequence chosen from SEQ ID No.: 1 SEQ ID No.: 2, SEQ ID No.: 3, SEQ ID No.: 4, SEQ ID No.: 5, SEQ ID No.: 6, SEQ ID No.: 7, SEQ ID No.: 8, SEQ ID No.: 9 and SEQ ID No.: 10.

Advantageously, the isolated polypeptide with phloroglucinol synthase activity is chosen from the isolated polypeptide with phloroglucinol synthase activity PHLD.Tp of *Tsukamurella paurometabola*, the isolated polypeptide with phloroglucinol synthase activity PHLD.Tt of *Tsukamurella tyrosinosolvens*, the isolated polypeptide with phloroglucinol synthase activity PHLD.Tps of *Tsukamurella pseudospumae*, the isolated polypeptide with phloroglucinol synthase activity PHLD.Tpu of *Tsukamurella pulmonis*, the isolated polypeptide with phloroglucinol synthase activity PHLD.Tp of *Tsukamurella* sp. 1534, the isolated polypeptide with phloroglucinol synthase activity PHLD.Nf of *Nocardia farcinica*, the isolated polypeptide with phloroglucinol synthase activity PHLD.Mma of *Mycobacterium marinum*, the isolated polypeptide with phloroglucinol synthase activity PHLD.Mk of *Mycobacterium kansasii*, the isolated polypeptide with phloroglucinol synthase activity PHLD.Mt of *Mycobacterium tuberculosis* and the isolated polypeptide with phloroglucinol synthase activity PHLD.Gh of *Gordonia hydrophobica*.

Isolated Nucleic Acid Molecules

The present invention relates to isolated nucleic acid molecules encoding at least one polypeptide chosen from type III polyketide synthases from bacteria, in particular type III polyketide synthases from actinomycete bacteria.

Advantageously, said polypeptide is as defined above.

According to one embodiment, the isolated nucleic acid molecule comprises a promoter controlling the expression of at least one nucleic acid sequence encoding a polypeptide as defined above. Thus, according to one embodiment, the present invention relates to an isolated nucleic acid molecule comprising at least one nucleic acid sequence encoding a polypeptide chosen from the type III polyketide synthases as defined above and also comprising a promoter controlling the expression of said at least one nucleic acid sequence.

Advantageously, the promoter is an exogenous promoter, in particular a yeast promoter, preferably a promoter chosen from ADH2 (pADH2) and CCW12 (pCCW12), more preferably a promoter chosen from ADH2 (pADH2) of *Saccharomyces cerevisiae* and CCW12 of *S. cerevisiae*, more preferably a promoter chosen from ADH2 of SEQ ID No.: 13 and CCW12 of SEQ ID No.: 14.

According to one embodiment, the isolated nucleic acid molecule comprises a transcription terminator for at least one nucleic acid sequence encoding a polypeptide as defined above. Thus, according to one embodiment, the present invention relates to an isolated nucleic acid molecule comprising at least one nucleic acid sequence encoding a polypeptide chosen from the type III polyketide synthases as defined above and also comprising a terminator controlling the expression of said at least one nucleic acid sequence.

Advantageously, the terminator is an exogenous terminator, in particular a yeast terminator, preferably the RPL3 terminator (tRPL3), more preferably the RPL3 terminator of *S. cerevisiae*, more preferably the RPL3 terminator of SEQ ID No.: 15.

According to one preferred embodiment, the isolated nucleic acid molecule comprises both a promoter and a terminator which are as defined above. Thus, according to one embodiment, the present invention relates to an isolated nucleic acid molecule comprising at least one nucleic acid sequence encoding a polypeptide chosen from the type III polyketide synthases as defined above and also comprising a promoter and a terminator controlling the expression of said at least one nucleic acid sequence.

According to one embodiment, the nucleic acid molecule also comprises an export sequence. Advantageously, this export sequence allows the secretion or excretion of the polypeptide(s) encoded by said nucleic acid molecule, in the cell medium.

According to one embodiment, the nucleic acid molecule is isolated from homologous strains in culture, preferably chosen from *Tsukamurella* sp., *Nocardia* sp., and *Mycobacterium* sp., in particular *Tsukamurella pourometabola*, *Tsukamurella tyrosinosolvens*, *Tsukamurella pseudospumae*, *Tsukamurella pulmonis*, *Tsukamurella* sp. 1534, *Nocardia farcinica*, *Mycobacterium marinum*, *Mycobakterium kansasii*, *Mycobacterium tuberculosis* and *Gordonia hydrophobica*.

According to one embodiment, the nucleic acid molecule is isolated from a heterologous vector or host cell comprising said molecule, said vector or said host cell being as defined above and as described below in the sections "Host cells" or "Vectors".

According to one embodiment, the isolated nucleic acid molecule is synthesized in vitro by means of nucleic synthesis techniques that those skilled in the art know perfectly well how to define.

According to one embodiment, the isolated nucleic acid molecule is recombinant.

Vectors

The present invention relates to vectors comprising at least one nucleic acid molecule as defined above.

Advantageously, the vector is a plasmid.

The vectors that are suitable in the context of the present invention comprise, without limitation, bacteriophage, plasmid or cosmid vectors for expression in prokaryotic host cells such as bacteria (for example *E. coli*, or bacteria of the *Pseudomonas* genus); vectors for expression in yeast (for example *Saccharomyces cerevisiae*, *Schyzosaccharomyces pombe*, *Pichia pastoris*); baculovirus vectors for expression in insect cell systems (for example, Sf 9 cells); viral and plasmid vectors for expression in plant cell systems (for example, the Ti plasmid, the cauliflower mosaic virus CaMV, the tobacco mosaic virus TMV); and also viral and plasmid vectors for expression in higher eukaryotic cells or organisms.

These vectors are generally commercially available (for example, from suppliers such as Invitrogen, Stratagene, Amersham Biosciences, Promega, etc.), available from deposit institutions such as the American Type Culture Collection (ATCC, Rockville, Md.), or have been the subject of numerous publications describing their sequence, their structures and the methods for producing them, so that those skilled in the art can apply them without difficulty.

Representative examples of suitable plasmid vectors comprise, without limitation, pREP4, pCEP4 (Invitrogen), pCI (Promega), pVAX (Invitrogen) and pgWiz (Gene Therapy System Inc).

Host Cells

In another aspect, the present invention relates to host cells comprising at least one nucleic acid molecule or at least one vector as defined above.

According to various embodiments, said host cell, in particular said heterologous host cell mentioned above, can be a prokaryotic cell, a lower eukaryotic cell such as a yeast cell, and other eukaryotic cells such as insect cells, plant cells and mammalian cells (for example human or nonhuman cells, preferably nonhuman cells).

Advantageously, the host cell is a microorganism selected from bacteria, yeasts, fungi, algae and cyanobacteria.

The host cell is preferably a yeast, said yeast being in particular selected from the *Saccharomyces*, *Candida*, *Ashbya*, *Dekkera*, *Pichia* (*Hansenula*), *Debaryomyces*, *Clavispora*, *Lodderomyces*, *Yarrowia*, *Zigosaccharomyces*, *Schizosaccharomyces*, *Torulaspora*, *Kluyveromyces*, *Brettanomycces*, *Cryptococcus* and *Malassezia* genera.

Even more particularly, the yeast is selected from the species *Saccharomyces cerevisiae*, *Saccharomyces boulardii*, *Saccharomyces douglasii*, *Saccharomyces bayanus*, *Zigosaccharomyces bailii*, *Schizosaccharomyces pombe*, *Dekkera brucelensis*, *Dekkera intermedia*, *Brettanomycces custersii*, *Brettanomycces intermedius*, *Kluyveromyces themotolerens*, *Torulaspora globosa* and *Torulaspora glabrata*.

Even more particularly, the yeast is of the *Saccharomyces* genus, preferably of the species *Saccharomyces cerevisiae*.

According to one embodiment, the host cell comprises at least one copy of the nucleic acid molecule as defined above, integrated into its genome.

According to one embodiment, the host cell comprises a single copy of the nucleic acid molecule as defined above, integrated into its genome.

When the host cell is a yeast cell, the copy or copies of the nucleic acid molecule can be integrated at various loci, preferentially at the URA3 locus, at the JLP1 locus, at the LEU2 locus, or at the TRP1 locus of the genome of said yeast cell. When the host cell is a yeast cell and several copies of the nucleic acid molecule are integrated, the various copies can be integrated at the same locus, or else at different loci, preferentially at any one of the combinations of the URA3, JLP1, LEU2 and/or TRP1 loci.

Advantageously, the codons used in the nucleic acid molecule have been adapted for optimal expression in the host cell selected.

An optimal expression can in particular be obtained when the codons chosen are those preferentially used by the organism of origin of the host cell. The preferentially used codons are known for most organisms commonly used in the field. Those skilled in the art will be able to easily determine the most advantageous codons to be used as a function of the host cell chosen.

To this effect, those skilled in the art know which technique to use in order to modify the codons of the nucleic acid molecule. The codons can for example be modified by in vitro site-directed mutagenesis using a sample of the nucleic acid molecule of which the codons are to be adapted, by means of an amplification by polymerase chain reaction (PCR). Alternatively, the nucleic acid molecule can be synthesized in vitro directly with the optimized codons.

The host cells can be cultured in small-scale and large-scale, aerobic or anaerobic bioreactors, in flasks or in Petri dishes. The culture can be performed at a temperature, at a pH, in a culture medium and at an oxygen content that are suitable for a given host cell.

Methods

Method for Producing a Polypeptide with Phloroglucinol Synthase Activity

The present invention also relates to a method for producing a polypeptide with phloroglucinol synthase activity as defined above.

According to one embodiment, the method for producing a polypeptide with phloroglucinol synthase activity as defined above comprises at least the steps consisting in:
(i) introducing a nucleic acid molecule or a vector as described above into a suitable host cell in accordance with the preceding description; and
(ii) culturing, in vitro, said host cell obtained in step (i) under conditions which allow the growth of said host cell and/or the expression of said nucleic acid molecule, so as to produce said polypeptide.

According to another embodiment, the method for producing a polypeptide with phloroglucinol synthase activity as defined above comprises at least the step consisting in:
(i) culturing, in vitro, a host cell expressing said polypeptide, for example a host cell as described above, under conditions which allow the growth of said host cell and/or the expression of the nucleic acid molecule contained in said host cell, so as to produce said polypeptide.

According to one possible embodiment, the method for producing a polypeptide with phloroglucinol synthase activity comprises at least one additional step chosen from the steps consisting in:
(α) recovering the cells expressing said polypeptide, obtained after the culturing step; and
(β) purifying the polypeptide from the cells recovered in step (α).

Method for Producing Phloroglucinol

The present invention also relates to a method for producing phloroglucinol.

According to one embodiment M1, the method for producing phloroglucinol comprises at least the steps consisting in:
(i) obtaining cells by implementing one of the methods described above;
(ii) bringing the cells obtained in step (i) into contact with a suitable substrate;
(iii) incubating the mixture resulting from step (ii) under conditions suitable for producing phloroglucinol;
(iv) optionally, recovering the reaction medium comprising the phloroglucinol, obtained after step (iii); and
(v) optionally, purifying the phloroglucinol from the reaction medium of step (iv).

According to another embodiment M2, the method for producing phloroglucinol comprises the steps consisting in:
(i) bringing a host cell expressing the polypeptide with phloroglucinol synthase activity as defined above, for example a host cell as defined above, into contact with a suitable substrate;
(ii) culturing, in vitro, the host cell of step (i) under conditions which allow the growth of said host cell and/or the expression of the nucleic acid molecule contained in said host cell, so as to produce phloroglucinol;
(iii) optionally, recovering the culture medium comprising the phloroglucinol, obtained after step (ii); and
(iv) optionally, purifying the phloroglucinol from the culture medium of step (iii).

For the purposes of methods M1 and M2, the substrate is a carbon source. Advantageously, the carbon source is a pure carbon source or an industrial coproduct (such as molasses or green syrup, for example from the sugar industry). Preferably, the substrate in the pure carbon source or the industrial coproduct is a simple sugar, such as glucose (or dextrose), fructose, galactose, mannose, sucrose, lactose or maltose; a complex sugar, such as a monosaccharide, a disaccharide or trisaccharides, or else a polysaccharide such as starch; an alcohol, such as ethanol; an acid; a fatty acid and the ester derivative thereof; or a mixture of sugars, of alcohols, of acids and/or of fatty acids or the ester derivatives thereof.

Preferably, the substrate is glucose. Alternatively, the substrate is ethanol.

According to another embodiment M3, the method for producing phloroglucinol comprises at least the steps consisting in:
(i) bringing at least one polypeptide obtained in step (β) of the method as described above into contact with a suitable substrate;
(ii) incubating the mixture resulting from step (i) under conditions suitable for producing phloroglucinol;
(iii) optionally, recovering the reaction medium comprising the phloroglucinol, obtained after step (ii); and
(iv) optionally, purifying the phloroglucinol from the reaction medium of step (iii).

According to another embodiment M4, the method for producing phloroglucinol comprises at least the steps consisting in:
(i) bringing at least one polypeptide as defined above into contact with a suitable substrate;
(ii) incubating the mixture resulting from step (i) under suitable conditions for producing phloroglucinol;
(iii) optionally, recovering the reaction medium comprising the phloroglucinol, obtained after step (ii); and
(iv) optionally, purifying the phloroglucinol from the reaction medium of step (iii).

For the purposes of these methods M3 and M4, the substrate is a thioester. Advantageously, the substrate is an acyl-Coenzyme A (or acyl-CoA) such as malonyl-CoA, acetyl-CoA, hexanoyl-CoA, decanoyl-CoA, lauroyl-CoA and palmitoyl-CoA, or a mixture thereof. Preferably, the substrate is malonyl-CoA.

According to one preferred embodiment, the purification of the phloroglucinol is carried out by liquid-liquid extraction.

The examples which follow aim to illustrate the present invention without any limitation. The enzymes respectively encoded by the PHLD gene of *Pseudomonas fluorescens* (Zha et al., 2006), and by the PKS1 gene of *Ectocarpus siliculosus* (Meslet-Cladière et al., 2013) are used therein as controls.

EXAMPLES

Example 1: Identification of New Candidate Phloroglucinol Synthases

Up until the present invention, only two phloroglucinol synthases had been identified and characterized:
- the enzyme encoded by the PHLD gene of *Pseudomonas fluorescens* (Zha et al., 2006), and
- the enzyme encoded by the PKS1 gene of *Ectocarpus siliculosus* (Meslet-Cladière et al., 2013).

The inventors have now discovered and characterized new phloroglucinol synthases using genetic and functional analyses.

As indicated in the introduction above, the exact functional characterization of a polyketide synthase is complex since this class of enzymes groups together proteins having high sequence similarities although they can catalyse substantially dissimilar reactions and recognize entirely different substrates.

1.1. Selection of New Candidate Enzymes

In order to identify new phloroglucinol synthases, the inventors identified sequences encoding putative type III polyketide synthases. The sequences of these putative type III polyketide synthases thus identified by the inventors were analysed and aligned with respect to one another using in particular as a basis the type III polyketide synthase alignment published by Meslet-Cladière et al. 2013.

The analysis of this sequence alignment resulted in the selection of a group of candidate enzymes, the protein sequences of which are close to that of the product of the PKS1.Es gene of the alga *Ectocarpus siliculosus* (Tables 1 and 2).

TABLE 1

Putative type III polyketide synthases identified. The shaded rows show the enzymes which have a known phloroglucinol synthase activity.

| Name | Reference in the databases | Known or putative function | Species | Kingdom |
|---|---|---|---|---|
| PHLD. Pf | AAY95147.1 | PhlD type III polyketide synthase | *Pseudomonas fluorescens* Pf-5 | Gammaproteobacteria/ pseudomonals (bacteria) |
| PKS1. Es | CBN76919.1 | III polyketide synthase without signal peptide 2-32 | *Ectocarpus siliculosus* | Ochrophytes (algae) |
| PHLD. Tp | WP_ 013126955.1 | polyketide synthase | *Tsukamurella paurometabola* | Actinobacteria/ tsukamurella (bacteria) |
| PHLD. Tt | WP_ 068525790.1 | polyketide synthase | *Tsukamurella tyrosinosolvens* | Actinobacteria/ tsukamurella (bacteria) |
| PHLD. Tps | WP_ 068569959.1 | polyketide synthase | *Tsukamurella pseudospumae* | Actinobacteria/ tsukamurella (bacteria) |
| PHLD. Tpu | WP_ 068567598.1 | polyketide synthase | *Tsukamurella pulmonis* | Actinobacteria/ tsukamurella (bacteria) |
| PHLD. Tsp | WP_ 019202763.1 | polyketide synthase | *Tsukamurella* sp. 1534 | Actinobacteria/ tsukamurella (bacteria) |
| PHLD. Nf | WP_ 011211464.1 | polyketide synthase | *Nocardia farcinica* | Actinobacteria/ corynebacteria (bacteria) |
| PHLD. Mma | WP_ 012393954.1 | polyketide synthase | *Mycobacterium marinum* | Actinobacteria/ corynebacteria (bacteria) |
| PHLD. Mk | ZP_ 04749411.1 | polyketide synthase | *Mycobacterium kansasii* ATCC 12478 | Actinobacteria/ corynebacteria (bacteria) |
| PHLD. Mt | WP_ 031677738.1 | polyketide synthase | *Mycobacterium tuberculosis* | Actinobacteria/ corynebacteria (bacteria) |
| PHLD. Gh | WP_ 066172590.1 | polyketide synthase | *Gordonia hydrophobica* | Actinobacteria/ actinomycetales (bacteria) |

TABLE 2

Protein sequences of the putative type III polyketide synthases identified

| SEQ ID No.: | Name | Protein sequence |
|---|---|---|
| SEQ ID NO: 1 | PHLD.Tp | MIAPQIRLGEPDTTPLPDPLWHGAPPAPPTTVAVIESLATGSPAQAHGQSVSAERV AARFADPIQAERIRRVYANTAVATRHLAIDPLSDDFADFSARPDTIRQRMDLYFEHA APLAIETARRALGAVDATEVGQLIFVTSTGFLAPGVDVAVTRSLGLPASTSRVVINFM GCAAAMNALRVASDFVRAHPDRKSLLVCLELSSVNAVFAGDPNDVVISSLFADGCG AALIGASEVGHPLPAGHIVVRDTFAHLLDDAEDGIVLGVNANGITCELAHSLPRYILD GVSPVIDGVLARNGLGREDVAHWAIHPGGPKIIESASAALGLPRSASQTSWAVLAE HGNMLSVSLLFVLERLLGARAAGGTQETGLAFSFAPGVTVEGFLFDVVGGPS |
| SEQ ID NO: 2 | PHLD.Tt | MTMNAGSQGAPALDVPAPVLPAPGTWLGAPPAPPTSVAVIESLATGSPAQTYGQ AESADRVAARFDDPRQAERIRRVYAKTRVDERHLAIDPLTPEFAEFSTRPDTVRERM DLFYEHAAPLAVDTARRALGVGTEHEFDPADVGQLVFVTSTGFLAPGVDVAVIRAL GLAPQTSRVVINFMGCAAAMNALRVSTDYVRAHPDRKSLMICLELSSVNAVFSGDP NDVVISSLFADGCGAAVIGASEVGHPLPGGRIVVRDTFTHLLDGAEDGIVLGVNANG ITCELAESLPQYIVDGVAPVIDEVLGRNDLGREAVAHWAIHPGGPKIIESAATALGLP DEASRTSWDVLAEHGNMLSVSLLFVLERLLAQVADGAATQPDGAPTTGMAFSFAP GVTVEGFLFDVVTGDQPGE |

TABLE 2-continued

Protein sequences of the putative type III polyketide synthases identified

| SEQ ID No.: | Name | Protein sequence |
|---|---|---|
| SEQ ID NO: 3 | PHLD.Tps | MAAPELPGTSVWRGAPPAPPTSVAVIESLATGSPSQAYDQAESADRVASRFDDPR QAERIRRVYAKTRVAERHLAIDPLTPEFAAFSTRPDTIRERMDLFFEHAAPLAIDTARR ALGTVDPADVGQLVFVTSTGFLAPGVDVAVIRALGLSPGTSRVVINFMGCAAAMN ALRVSTDYVRAHPDRKSLMICLELSSVNAVFSGDPNDVVISSLFADGCGAALIGASEV GHPLPAGNIVVRDTFSHLLDGAEDGIVLGVNADGITCELAESLPQYIVDGVAPVVDG VLRRNGLDRDAVAHWAIHPGGPKIIESASTALGLPDEASRLSWDVLAGHGNMLSVS LLFVLERLLAQVASDGADGAPSTGMAFSFAPGVTVEGFLFDVVTTGE |
| SEQ ID NO: 4 | PHLD.Tpu | MNTTEQQSVLPQQAWLGAPPAPPTSVAVIESLATSSPTQTYGQAESADRVAARFD DPRQAERIRRVYAKTRVTERHLAIDPLTPEFAEFSARPDTVRERMDLFFEHAAPLAIE TARRALGDNAATDIGQLVFVTSTGFLAPGVDVAVIRALGLAPQTSRVVINFMGCAA AMNALRVSTDYVRAQPDRKSLMICLELSSVNAVFSGDPNDVVISSLFADGCGAAVI GASEVGHPLPSGQIVVRDTFTHLLDGAEDGIVLGVNANGITCELAESLPQYIVNGVA PVVDAVLDRNGLGREAVAHWAIHPGGPKIIESAAAALGLPDDASRLSWDVLAEHG NMLSVSLLFVLERLRAQVASDGADGAPSTGMAFSFAPGVTVEGFLFDVVTTGE |
| SEQ ID NO: 5 | PHLD.Tsp | MNIQDRSTVAPDSPALGFPPAPPTSVAVIESLATGSPSGVHAQAESADRVASRFDD PAQAERIRRVYTKTRVARRHLAIDPLDEDFAAFSARPDTIRERMDLFAEHASPLAVDT ARRALGAVDPADVGQLVFVTSTGFLAPGVDVAIVRALGLPATTSRVIVNFMGCAAA MNALRVASDFVRAHPDRKSLMVCLELSSVNAVFSGDPNDVVISSLFADGCGAAVIG ASEVGHPLPGGSIVVRDTFAHLLDGAEDGIVLGVNANGITCELAESLPRYIVDGVRPV IDGVLARNGLGHADVAHWAIHPGGPKIIESASAALGLPAAASATSWQVLAEHGNM LSVSLLFVLERMLSGLPDGAPSTGMAFSFAPGVTVEGFLFDIVRDGAPRPGALGGRP A |
| SEQ ID NO: 6 | PHLD.Nf | MSITVDEGGARPATEPRQRIHPDLGHAHTPMPPAPPVTIGVVEGIATGSPAQIVDQ AEAAERVAALFTDPAQRARIARVYEKTRIETRRMAVDPTAPEFRSFSRQPGTLRERM NLFYRHAAPLAVDVAGRALADSGAAAADIGLLVFVTSTGFIAPGVDVAVLRELGLVP TVGRVVVNFMGCAAAMNGIRTGVDYVRAHPDKKALVVCLELSSVNAVFADDVND VIIHSLFGDGCGAVVLGASQARQPLAPGRVVVRDSFSHLFDAAEDGIVLGVDHNGIT CELSENLPRYIYRGVDPVVREVLARNGLRKSDIDLWAIHPGGPKIIEESVRSLGLSPEQ AAPSWDVLARHGNMLSVSLIFVLEQMIAQSATAEPISTGVAFSFAPGVTLEGLIFDII RR |
| SEQ ID NO: 7 | PHLD.Mma | MSTAAEGGAIRRAGHEPRYDLAQLPPAPPTTVAVIEGMATGAPQRVVAQADAAA RVSELFVDPQQRERISRIYDKTRIDTRRMAVDPLDDEFDEFRREPATIRDRMNLFYQ HAVPLAVDVAARALDGLPYAPDEIGQLVFVTSTGFIAPGVDVEIVKQLGLPRSISRVV VNFMGCAAAMNAIRTATNYVRAHPSMKALVVCIELSSVNAVFADDINDVVIHSLFG DGCGALVIGASQVQQPLAGNVVIRSSFSQLLDDSEDGIVLGVNHDGITCELSENLP SYIYRSVDPVVAEMLRDNGLSKADIDLWAIHPGGPKIIEQSARSLGIPVGRAVQSWD VLAQFGNMLSVSLIFVLEMMVAQAESDKPISTGVAFAFAPGVTVEGMLFDIIRR |
| SEQ ID NO: 8 | PHLD.Mk | MSSAADGGAPVADVPGYEPHYDLAQLPPAPPTTVAVIEGMATGVPQRVVRQSDA AARVAQMFVDPQQRERVSRVYAKTRIDTRRMAVNPLDAEFDAFRREPATIRDRMS LFYRHAVPLAVEVTRRALAGLSYGADEIGLLVFVTSTGFVAPGVDVAIVKELGLSRAIS RVVVNFMGCAAAMNAIRTATNYVRAHPAMKALVVCIELCSVNAVFADNVKDVVI HSLFGDGCAALVIGASQVQQQLPAGSVVIRSNFSQLLDDAEDGIVLGVNHDGITCEL SENLPDYIYRGVAPVVANVLYDNGLQQSDIDLWAIHPGGPKIIEQSVRSLGIGVECAA PSWDVLARYGNMLSVSLIFVLEMMVQQAESEKPLSTGVAFAFAPGVTVEGMLFDI VRR |
| SEQ ID NO: 9 | PHLD.Mt | MNVSAESGAPRRAGQRHEVGLAQLPPAPPTTVAVIEGLATGTPRRVVNQSDAADR VAELFLDPGQRERIPRVYQKSRITTRRMAVDPLDAKFDVFRREPATIRDRMHLFYEH AVPLAVDVSKRALAGLPYRAAEIGLLVATSTGFIAPGVDVAIVKELGLSPSFGDGCA ALVIGASQVQEKLEPGKVVVRSSFSQLLDNTEDGIVLGVNHNGITCELSENLPGYIFS GVAPVVTEMLWDNGLQISDIDLWAIHPGGPKIIEQSVRSLGISAELAAQSWDVLAR FGNMLSVSLIFVLETMVQQAESAKAISTGVAFAFGPGVTVEGMLFDIIRR |
| SEQ ID NO: 10 | PHLD.Gh | MPAPVTTVAVIEAVATGAPATVHPQTRAAEQVAELYDDPALQERIRRLYRNTRVQT RHLAVDPMTPEFQEFSSRPATVRTRMNDYFHHAVPLAVDVARRALAGVTDPATEI GQIIFVTSTGFIAPGVDVAVITELGLAPTVHRVIINFMGCAAAINGISTATDHVRANP DSRALLICLELSSVNAVFGADPVELVTHSLFGDGCGAMLIGASPVGRRLAPGQLVVR DTFSHLFHDTGDGIVLGVNDDGITCELAQELPSYIRRGVGPAIDAALNRSRLRRDDIA HWAIHPGGPAIIEQSVAALDLPPDRAATSWEVLAEYGNMLSVSLVFVLEKLIAAGAH GRGQAPETGVAFSFAPGVALEGMLFDLVC |

FIG. 1 presents the alignment of the protein sequences of the candidate enzymes listed in Table 1. The alignment of the ten candidate enzymes selected with the PKS1.Es enzyme was carried out using the Clustal W software.

Table 3 presents the matrix of the sequence identities that exist between these various candidate enzymes and PHLD.Pf and PKS1.Es.

TABLE 3

Matrix of the sequence identities that exist between the various candidate enzymes.

|  | PHLD.Tt | PHLD.Tp | PHLD.Tps | PHLD.Tpu | PHLD.Tsp | PHLD.Nf | PHLD.Mma | PHLD.MK | PHLD.Mt | PHLD.Gh | PHLD.Pf | PKS1.Es |
|---|---|---|---|---|---|---|---|---|---|---|---|---|
| PHLD.Tt | ID | 74.7 | 84.2 | 85.4 | 75.7 | 58.2 | 55.8 | 55.3 | 44.6 | 55.8 | 19.3 | 36.3 |
| PHLD.Tp | 74.7 | ID | 76.3 | 76 | 76.5 | 55.4 | 55 | 54.7 | 42.7 | 58.4 | 21.3 | 34 |
| PHLD.Tps | 84.2 | 76.3 | ID | 87.2 | 77.9 | 57.6 | 57.7 | 56.3 | 45.2 | 58.3 | 20.4 | 37.3 |
| PHLD.Tpu | 85.4 | 76 | 87.2 | ID | 76.8 | 57.8 | 56.2 | 54.7 | 44.7 | 58.9 | 20.3 | 37 |
| PHLD.Tsp | 75.7 | 76.5 | 77.9 | 76.8 | ID | 56 | 56.3 | 55 | 45.3 | 54.8 | 19.9 | 35 |
| PHLD.Nf | 58.2 | 55.4 | 57.6 | 57.8 | 56 | ID | 67.5 | 67.2 | 55.5 | 55.7 | 19.1 | 35.9 |
| PHLD.Mma | 55.8 | 55 | 57.7 | 56.2 | 56.3 | 67.5 | ID | 82.7 | 65.6 | 54.9 | 19.9 | 35.8 |
| PHLD.Mk | 55.3 | 54.7 | 56.3 | 54.7 | 55 | 67.2 | 82.7 | ID | 66 | 52.8 | 19 | 35.4 |
| PHLD.Mt | 44.6 | 42.7 | 45.2 | 44.7 | 45.3 | 55.5 | 65.6 | 66 | ID | 44.3 | 15.1 | 27.7 |
| PHLD.Gh | 55.8 | 58.4 | 58.3 | 58.9 | 54.8 | 55.7 | 54.9 | 52.8 | 44.3 | ID | 21.1 | 35.9 |
| PHLD.Pf | 19.3 | 21.3 | 20.4 | 20.3 | 19.9 | 19.1 | 19.9 | 19 | 15.1 | 21.1 | ID | 23.1 |
| PKS1.Es | 36.3 | 34 | 37.3 | 37 | 35 | 35.9 | 35.8 | 35.4 | 27.7 | 35.9 | 23.1 | ID |

The results show that the phylogenetic distance that exists between the candidate enzymes and the bacterial enzyme PHLD.Pf is considerable since less than 25% identity is observed between these two groups. It is not therefore possible to assign, a priori, a phloroglucinol synthase function to the putative polyketide synthases studied because of this strong sequence divergence.

1.2. Measurement of the Phloroglucinol Synthase Activities in Yeast

In order to identify the phloroglucinol synthases among the candidates identified above, a method of extracting and assaying phloroglucinol was developed as detailed below.

1.2.1. Phloroglucinol Extraction Method

The method was developed using resorcinol as internal standard. Various tests resulted in the development of a liquid-liquid extraction method carried out at pH 4.0 in the presence of ethyl acetate as solvent, and by saturating the aqueous phase with NaCl. The extraction is carried out for 30 min with circular shaking. The organic phase is removed and the ethyl acetate solvent is evaporated off under a stream of nitrogen $N_2$ at 30° C. The dry extract obtained after complete evaporation is then taken up in a predetermined volume of a 50%-50% ethanol/$H_2O$ mixture.

The extraction yield was measured by mass spectrometry after high pressure chromatography on a C18 column (dimensions: 100 mm×2.1 mm; particle size: 1.7 µm) using a 0.03% methanoic acid (HCOOH)/acetonitrile (ACN) gradient.

The extraction yields were determined using solutions of phloroglucinol and resorcinol prepared in the culture medium used for the growth of the yeasts. The phloroglucinol concentrations correspond to the bottom (20 µg·ml$^{-1}$) and top (200 µg·ml$^{-1}$) points of the assay range. The resorcinol concentration corresponds to the concentration added as internal standard during the assays (200 µg·ml$^{-1}$). The results are presented in Table 4.

TABLE 4

Extraction yield for phloroglucinol (20 and 200 µg · ml$^{-1}$) and for resorcinol (200 µg · ml$^{-1}$), extracted with ethyl acetate, according to the method described

| Product | Phloroglucinol | | Resorcinol (EI) |
|---|---|---|---|
| Concentration of phloroglucinol or of resorcinol in the culture medium (µg · ml$^{-1}$) | 20 | 200 | 200 |
| YLD (%) | 76 | 89 | 82 |

1.2.2. Development of a UPLC/UV and UPLC/MS Analysis Method

A method of analysis by UPLC chromatography and UV (ultraviolet radiation) absorbance measurement was developed. The extract is chromatographed on a pentafluorophenyl propyl (PFP) column having the dimensions 100 mm×2.1 mm; particle size: 1.8 µm, according to a 0.1% HCOOH/ACN–0.1% HCOOH gradient. The phloroglucinol is detected by UV at 230 nm. A UPLC-mass spectrometry (UPLC/Mass) method was also developed.

The quantification is carried out using a range of 20 to 200 µg·ml$^{-1}$ of phloroglucinol diluted in yeast culture medium (Yeast Extract 1%, BactoPeptone 2%) in the presence of a fixed amount of resorcinol, used as internal standard. The amount of phloroglucinol is determined by calculating the surface ratios of the phloroglucinol/resorcinol chromatography peaks.

Figure 2:
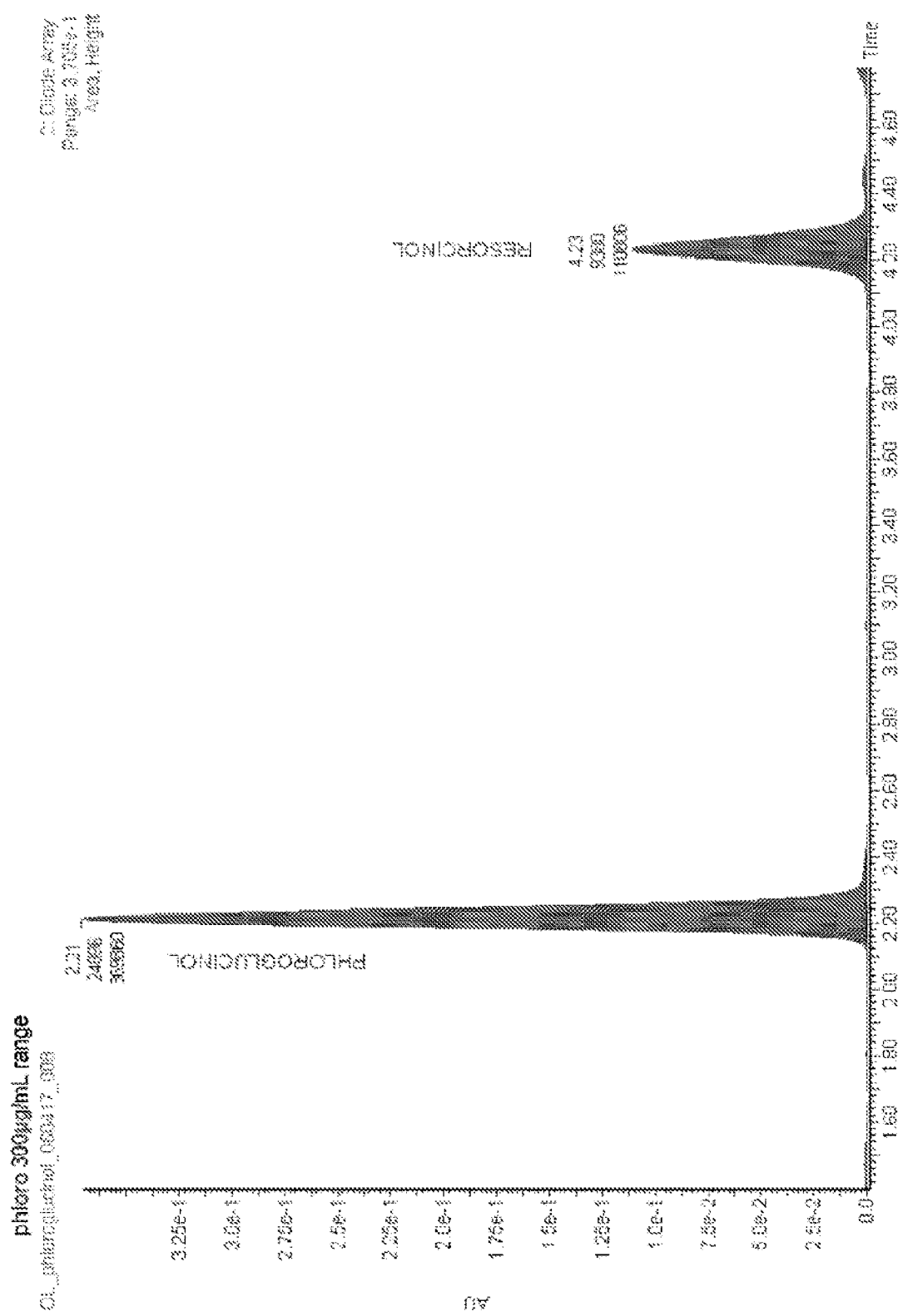
FIG. 2 presents an example of phloroglucinol/resorcinol separation on a propyl-pentafluorophenyl (PFP) column.

FIG. 2 presents an example of phloroglucinol/resorcinol chromatography peaks obtained on a PFP column.

This assay method thus makes it possible to reliably measure, qualitatively and quantitatively, the phloroglucinol present in a sample.

The UPLC-mass spectrometry (UPLC/mass) method makes it possible to assay the samples containing a phloroglucinol concentration ranging from 2 to 50 µg·ml$^{-1}$.

19

Example 2: Identification of New Functional Phloroglucinol Synthases 2.1. Expression of the Candidate Genes in the *Saccharomyces cerevisiae* Yeast in Multicopy Form The 10 candidate genes (PHLD.Tp, PHLD.Tt, PHLD.Tps, PHLD.Tpu, PHLD.Tsp, PHLD.Nf, PHLD.Mma, PHLD.Mk, PHLD.Mt and PHLD.Gh) selected and described above, and also the PHLD.Pf and PKS1.Es genes encoding the two phloroglucinol synthases identified to date, used as controls (see Tables 1 and 2), were synthesized by adapting the codons used for optimal expression in the *S. cerevisiae* yeast.

This codon adaptation was carried out in order to optimize the expression of these different genes in the yeast cells (these 12 synthetic genes encode proteins strictly identical to the proteins expressed by the organisms of origin). Each of these genes was placed under the control of the same yeast promoter ADH2 (pADH2) which allows their expression in particular when the culture medium contains ethanol as carbon source. The transcription terminator of the RPL3 yeast gene (tRPL3) was placed downstream of each of the 12 genes placed under the control of the ADH2 promoter.

FIG. 3 shows an example of a gene unit thus constructed for a candidate or a given control (PHLD.ii).

The various gene units thus constructed were independently integrated at the URA3 locus of the genome of a wild-type strain of the *S. cerevisiae* yeast. The wild-type strain used is the commercial strain W303 (genotype: MAT-a, his3, leu2, trp1, ura3, ade-). The integration technique used allows the integration of a variable number of copies of each gene unit. For each construct, the number of copies of gene units integrated was determined by quantitative PCR according to the conventional Taqman method.

The yeast strains expressing various numbers of copies of each of the 10 PHLD.ii candidate genes or of the PHLD.Pf and PKS1.Es control genes described above were cultured in the presence of 20 g·l$^{-1}$ of ethanol as carbon source for 48 hours at 30° C. The 12 yeast strains independently obtained after transformation and integration, at the URA3 locus, of the gene units described above were thus analysed for their capacity to produce phloroglucinol. The W303 wild-type parental strain was cultured under the same conditions and used as a control.

Figure 4C:
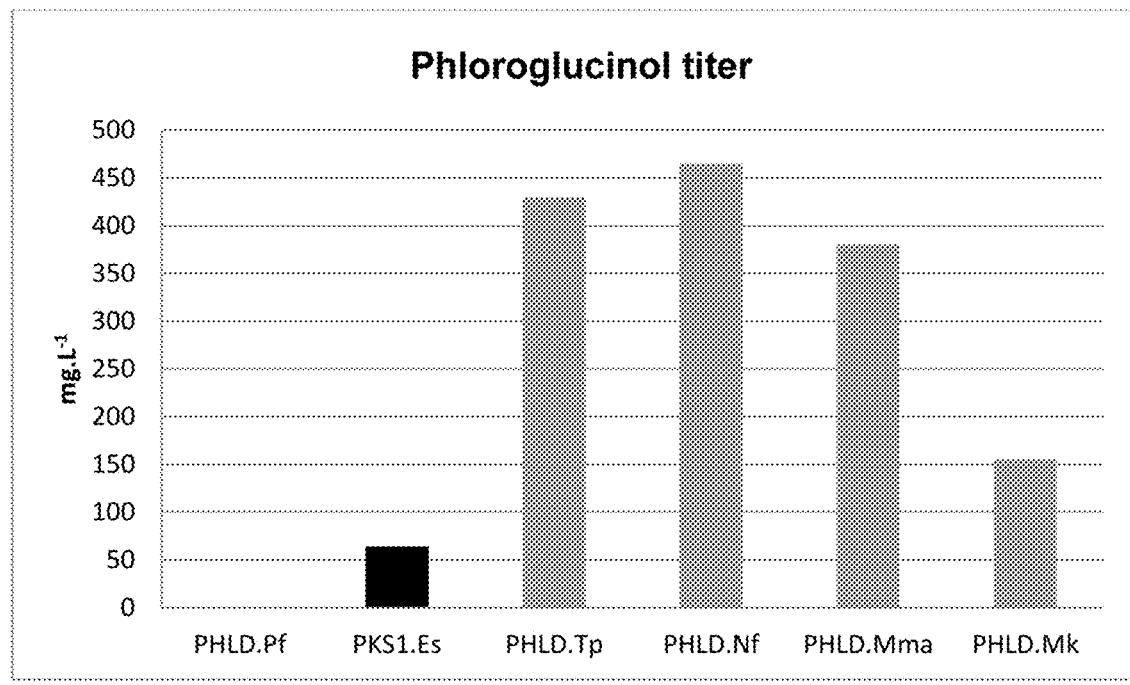
FIG. 4 shows the levels of phloroglucinol production in the yeast strains expressing the various candidate genes PHLD.ii and the control PHLD.Pf and PKS1.Es genes (several copies) under the control of the ADH2 promoter, after 48 hours of culture in a 24-well plate in the presence of 20 g·l$^{-1}$ of ethanol as carbon source at 30° C. (A) Summary of the various data measured. (B) Optical densities (OD) of the various cultures measured at 600 nm ($OD_{600}$), indicating the level of growth of each strain. (C) Level of phloroglucinol production (in mg·l$^{-1}$) measured in the culture medium. (D) Level of phloroglucinol production (in mg·l$^{-1}$) standardized relative to the number of copies of genes integrated into the genome.

The optical densities (ODs) of the various cultures were measured at 600 nm (OD$_{600}$), thus indicating the level of growth of each strain (FIGS. 4A and B).

The capacity of the various yeast strains expressing the various PHLD.ii genes under the control of the ADH2 promoter to synthesize phloroglucinol was tested using the extraction and assay method developed as described in section 1.2 above. The phloroglucinol production level (in mg·l$^{-1}$) was measured in the culture medium (FIGS. 4A and C).

Figure 4:
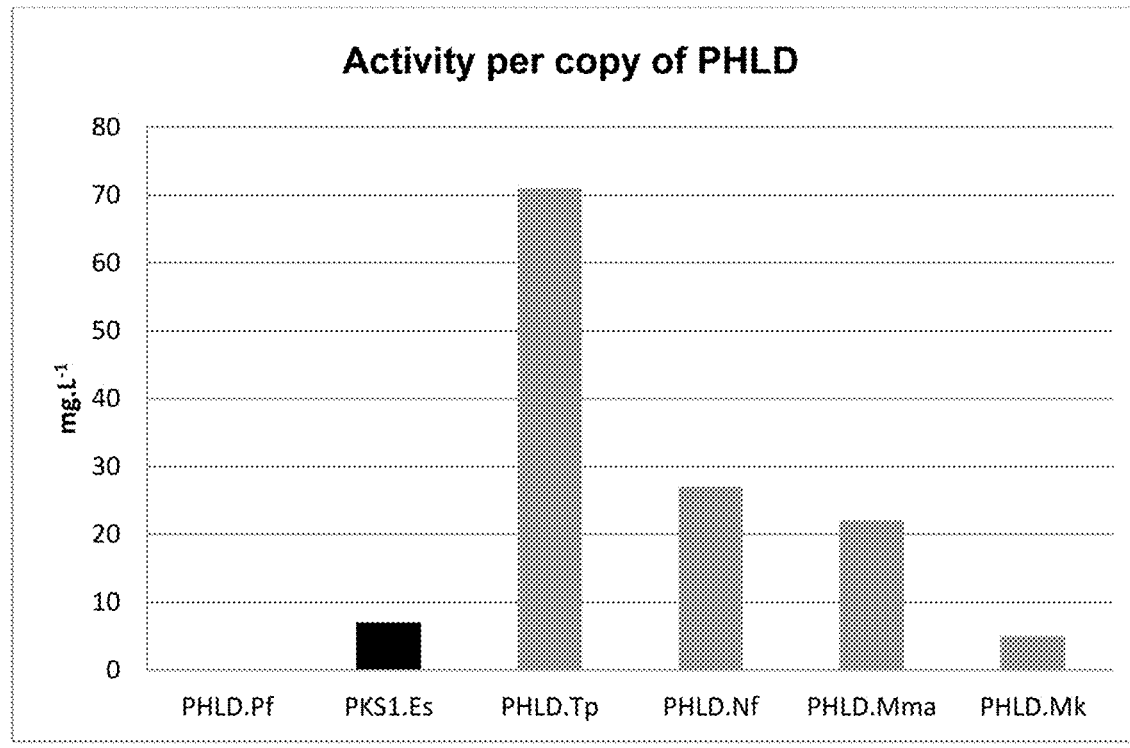

FIG. 4 shows that all of the strains expressing different numbers of copies of the PHLD.Tp, PHLD.Tt, PHLD.Tps, PHLD.Tpu, PHLD.Tsp, PHLD.Nf, PHLD.Mma, PHLD.Mk, PHLD.Mt and PHLD.Gh genes produce a significant amount of phloroglucinol which is excreted into the culture medium (FIGS. 4A, C and D). These results thus indicate that each of these 10 genes expresses a phloroglucinol synthase that is active in yeast.

Furthermore, as expected, no phloroglucinol production was measured in the W303 control parental strain (data not shown).

20

Thus, this functional study made it possible to identify ten new phloroglucinol synthases, encoded respectively by the PHLD.Tp, PHLD.Tt, PHLD.Tps, PHLD.Tpu, PHLD.Tsp, PHLD.Nf, PHLD.Mma, PHLD.Mk, PHLD.Mt and PHLD.Gh genes. This study reveals for the first time that Gram+ bacteria, in particular actinomycete bacteria encode functional phloroglucinol synthases (PHLD.Tp, PHLD.Tt, PHLD.Tps, PHLD.Tpu, PHLD.Tsp, PHLD.Nf, PHLD.Mma, PHLD.Mk, PHLD.Mt and PHLD.Gh).

This study also reveals for the first time that the PKS1.ES enzyme is functional when it is expressed in a heterologous eukaryotic system, namely yeast. This study also reveals, unexpectedly, that PHLD.Pf does not encode a phloroglucinol synthase that is functional in yeast. This result is surprising since the enzyme encoded by PHLD.Pf exhibits a phloroglucinol synthase activity demonstrated when it is expressed in *Escherichia coli* (Achkar et al., 2005).

2.2. Expression of the Candidate Genes in the *Saccharomyces cerevisiae* Yeast in the Form of a Single Copy The production of phloroglucinol by strains having integrated only a single copy of the PHLD candidate gene selected and identified as being functional in yeast (see the results of the preceding section and FIG. 4) was also evaluated. The PKS1.Es gene encoding phloroglucinol synthase that is functional in yeast according to the results described in section 2.1 above was used as positive control. The PHLD.Pf gene encoding phloroglucinol synthase that is not functional in yeast according to the results described in section 2.1 above was used as negative control.

Each of these genes was placed either under the control of the yeast promoter ADH2 (pADH2), which allows their expression in particular when the culture medium contains ethanol as carbon source, or under the control of the yeast promoter CCW12 (pCCW12), which allows their expression, in particular during glycolysis, when the culture medium contains glucose as carbon source. The transcription terminator of the RPL3 yeast gene (tRPL3) was placed downstream of each of the constructs.

Figures 5, 6A:
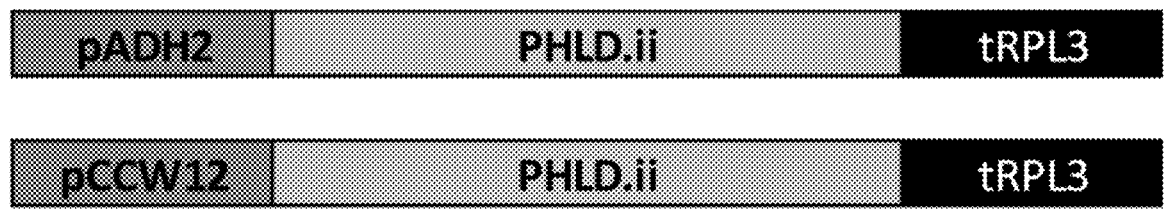
FIG. 5 shows the structure of the gene constructs integrated into the genome of the yeast at the JLP1 locus. The gene encoding each PHLD/PKS1 is under the control of the pADH2 promoter or of the pCCW12 promoter.

The details of the various gene constructs produced is reported in FIG. 5.

Figure 6B:
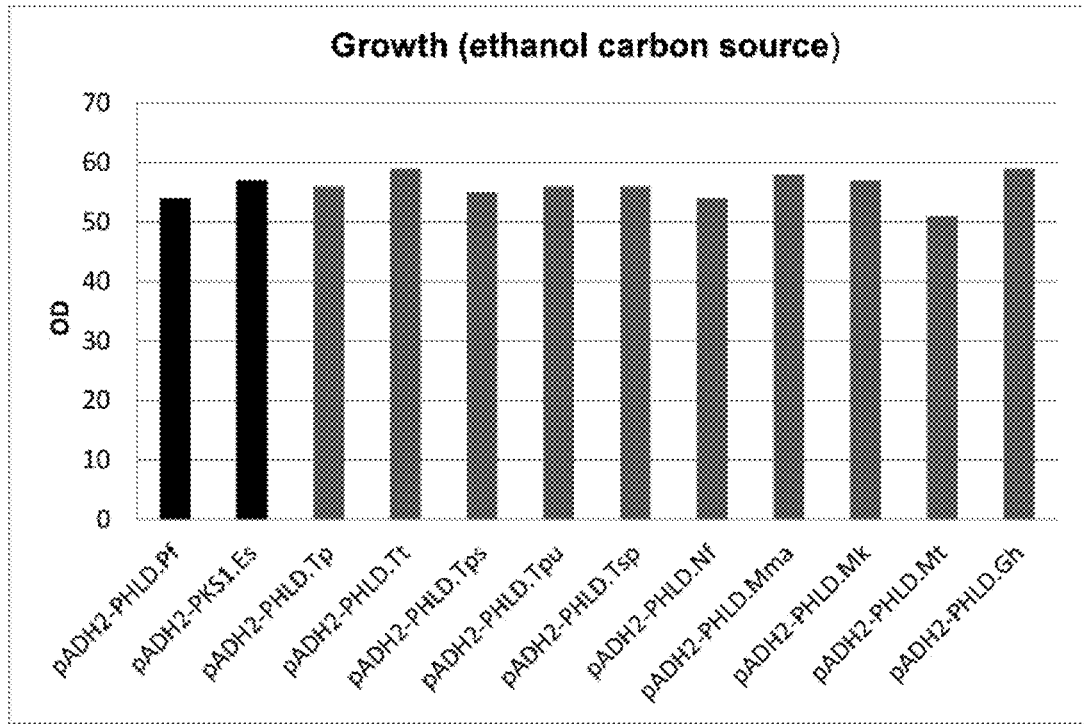
FIG. 6 shows the levels of phloroglucinol production in the yeast strains expressing the various PHLD.ii genes (only 1 copy) under the control of the ADH2 promoter after 48 hours of culture in a 24-well plate in the presence of 20 g·l$^{-1}$ of ethanol as carbon source at 30° C. (A) Summary of the various data measured. (B) Optical densities (OD) of the various cultures measured at 600 nm ($OD_{600}$), indicating the level of growth of each strain. (C) Level of phloroglucinol production (in mg·l$^{-1}$) measured in the culture medium.
Figure 6C:
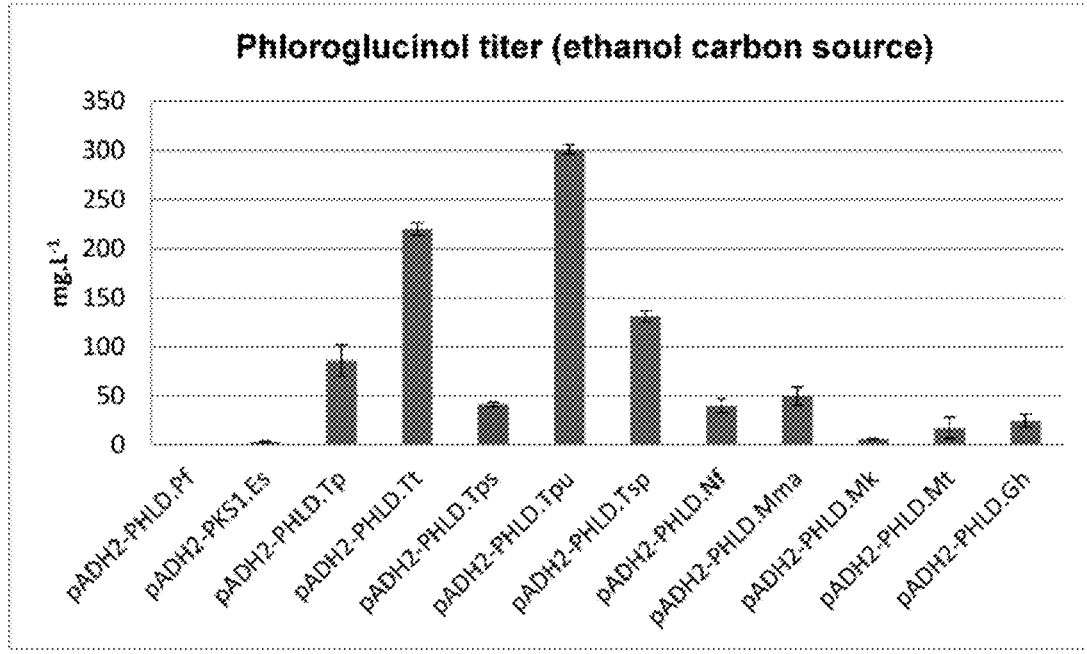

The yeast strains expressing a single copy of PHLD or of PKS1 were cultured in the presence of 20 g·l$^{-1}$ of ethanol as carbon source (constructs controlled by pADH2) or in the presence of 20 g·l$^{-1}$ of glucose (constructs controlled by pCCW12) for 48 hours at 30° C. (FIGS. 6 and 7). The strains were cultured and analysed for their capacity to produce phloroglucinol.

Figures 7A, 7B:
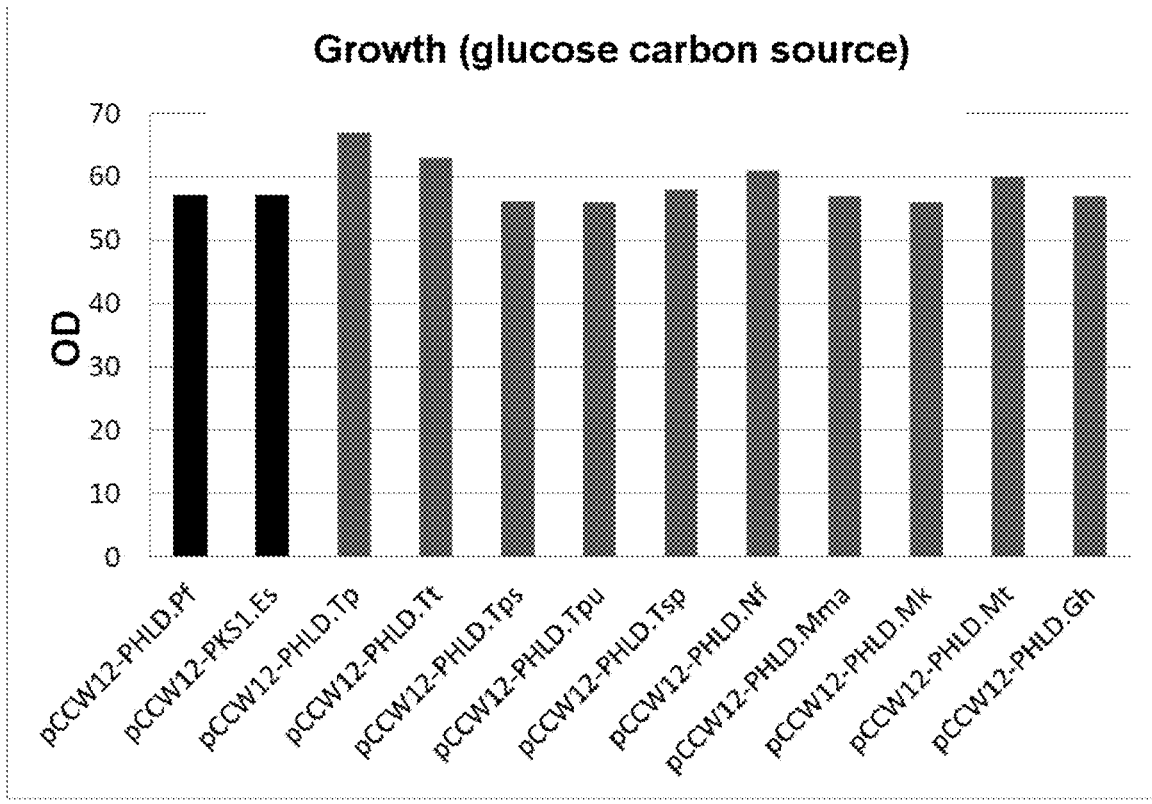
FIG. 7 shows the levels of phloroglucinol production in the yeast strains expressing the various PHLD genes (only 1 copy) under the control of the CCW12 promoter after 48 hours of culture in a 24-well plate in the presence of 20 g·l$^{-1}$ of glucose as carbon source at 30° C. (A) Summary of the various data measured. (B) Optical densities (OD) of the various cultures measured at 600 nm ($OD_{600}$), indicating the level of growth of each strain. (C) Level of phloroglucinol production (in mg·l$^{-1}$) measured in the culture medium.
Figure 7C:
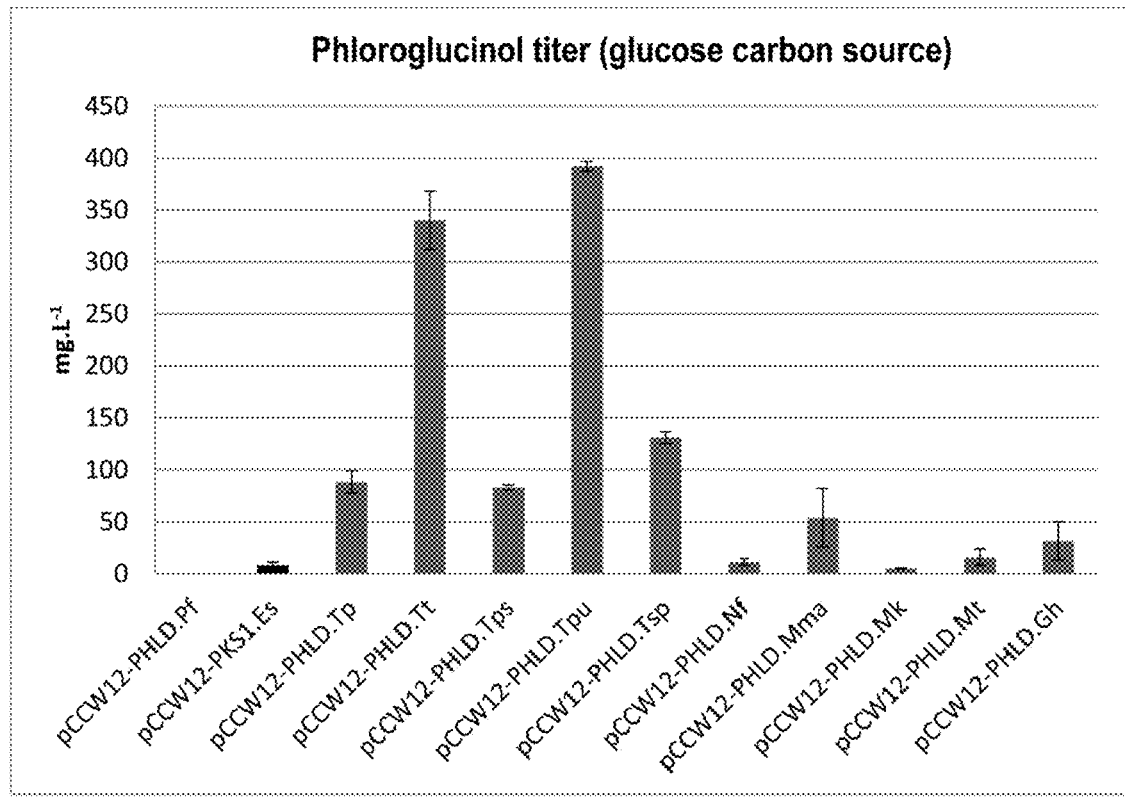

The optical densities of the various cultures were measured at 600 nm (indicating the level of growth of each strain, FIGS. 6A and B and FIGS. 7A and B) and the phloroglucinol production (in mg·l$^{-1}$) was measured in the culture medium, for 2 independent transformants for each construct (FIGS. 6A and C and FIGS. 7A and 9C).

FIG. 6 (A and C) shows that the strains expressing a single copy of the PHLD.Tp, PHLD.Tt, PHLD.Tps, PHLD.Tpu, PHLD.Tsp, PHLD.Nf, PHLD.Mma, PHLD.Mk, PHLD.Mt or PHLD.Gh genes under the control of the ADH2 promoter synthesize a measurable and significant amount of phloroglucinol which is excreted into the culture medium, in the presence of ethanol as carbon source.

For the cultures carried out in the presence of glucose as carbon source, the strains expressing a single copy of the PHLD.Tp, PHLD.Tt, PHLD.Tps, PHLD.Tpu, PHLD.Tsp, PHLD.Nf, PHLD.Mma, PHLD.Mk, PHLD.Mt and PHLD.Gh genes under the control of the CCW12 promoter all synthesize phloroglucinol, in an amount that is comparable to the cultures carried out in the presence of ethanol as carbon source (FIGS. 7A and C).

The results obtained above confirm the results obtained in the strains containing several copies of the phloroglucinol synthases described in section 2.1 above. Thus, the expression of the PHLD.Tp, PHLD.Tt, PHLD.Tps, PHLD.Tpu, PHLD.Tsp, PHLD.Nf, PHLD.Mma, PHLD.Mk, PHLD.Mt and PHLD.Gh candidate enzymes results in the significant production of phloroglucinol by the yeast cells. These results show that these genes encode phloroglucinol synthases and that these phloroglucinol synthases are active in yeast cells.

These results additionally show that the levels of phloroglucinol production are high even when a single copy of the gene encoding the phloroglucinol synthase is expressed.

These results are the first demonstrations of the existence of a phloroglucinol synthase activity in the gram+ type bacteria.

More generally, the results show that the PHLD.ii candidate enzymes tested exhibit an activity that overall is higher than the only two phloroglucinol synthases known before this study, i.e. the enzymes of E. siliculosus and P. fluorescens. The PHLD candidate enzymes of the Tsukamurella genus (PHLD.Tt, PHLD.Tps, PHLD.Tpu, PHLD.Tsp, PHLD.Tp) are particularly active when they are expressed in yeast. Indeed, the phloroglucinol production standardized by the number of copies demonstrates that the Tsukamurella enzymes tested (PHLD.Tp, PHLD.Tt, PHLD.Tpu, PHLD.Tps and PHLD.Tsp) have a phloroglucinol synthase activity that is at least 10 times higher than that of the PKS1 enzyme of Ectocarpus siliculosus in the expression system in yeast tested herein. According to these results, the PHLD.Tpu enzyme appears in particular to be the most active enzyme, under the various conditions tested.

The 3 enzymes PHLD.Mma (of Mycobacterium marinum), PHLD.Nf (of Nocardia farcinica) and PHLD.Gh (of Gordonia hydrophobica) are also significantly very active.

The present invention thus provides several new original and advantageous pathways for the biosynthesis of phloroglucinol in yeast.

2.3. Additional Observations

The study carried out by the inventors and reported here made it possible to identify 10 new enzymes having a phloroglucinol synthase activity. These 10 new phloroglucinol synthases come from gram+ bacteria of the order Actinomycetales, including the Tsukamurella genus (PHLD.Tt, PHLD.Tps, PHLD.Tpu, PHLD.Tsp, PHLD.Tp), the Nocardia genus (PHLD.Nf); the Mycobacterium genus (PHLD.Mma, PHLD.Mt and PHLD.Mk) and the Gordonia genus (PHLD.Gh) and have never been described up until now as producing phloroglucinol.

These results therefore demonstrate for the first time and unequivocally that it is possible to synthesize phloroglucinol in yeast cells.

It is important to note that the phloroglucinol synthesized is more than 95% secreted into the culture medium by the yeast cells. This particularly efficient secretion is very favourable to the implementation of a phloroglucinol bioproduction process.

The phloroglucinol synthases of the actinomycete bacteria of the Tsukamurella genus appear to be the most active according to the results obtained to date. Indeed, the results obtained show that the PHLD enzymes of Tsukamurella sp., expressed in yeast cells, are at least 10 times more active than the phloroglucinol synthase of the brown alga Ectocarpus siliculosus of the prior art, under the conditions tested.

The PHLD enzymes of Tsukamurella sp. could thus represent enzymes of choice for implementing a process of phloroglucinol bioproduction in the yeast S. cerevisiae.

Finally, the enzymes identified by the inventors are original in terms of species of origin and in terms of protein sequences. Indeed, it is shown for the first time that Gram+ bacteria encode functional phloroglucinol synthases. In addition, the protein sequence of the enzyme that is the most active under the experimental conditions tested by the inventors, PHLD.Tpu of Tsukamurella pulmonis, differs significantly from the sequence of the known PKS1.Es enzyme of Ectocarpus siliculosus (difference of more than 63%, Table 3).

LITERATURE REFERENCES

Achkar J et al., (2005) "Biosynthesis of phloroglucinol" J Am Chem Soc. 127:5332-5333. Meslet-Cladière L, Delage L, Leroux C J, Goulitquer S, Leblanc C, Creis E, Gall E A, Stiger-Pouvreau V, Czjzek M, and Potin P. (2013) "Structure/function analysis of a type III polyketide synthase in the brown alga Ectocarpus siliculosus reveals a biochemical pathway in phlorotannin monomer biosynthesis." Plant Cell. 25:3089-3103.

Zha W, Rubin-Pitel S B and Zhao H. (2006) "Characterization of the substrate specificity of PHLD, a type III polyketide synthase from Pseudomonas fluorescens." J Biol Chem. 281:32036-32047.

The invention claimed is:

1. A method for producing phloroglucinol, the method comprising:
   (i) contacting, with a suitable substrate, a host cell expressing at least one polypeptide with phloroglucinol synthase activity, wherein said at least one polypeptide is a type III polyketide synthase of a bacteria of *Tsukamurella* genus, wherein the suitable substrate is a carbon source; and
   (ii) growing, in vitro, the host cell of step (i) under conditions which allow the growth of said host cell, the expression of the polypeptide with phloroglucinol synthase activity contained in said host cell, or both the growth of said host cell and the expression of the polypeptide with phloroglucinol synthase activity contained in said host cell, so as to produce phloroglucinol, wherein said polypeptide comprises an amino acid sequence having at least 95% identity with a sequence selected from the group consisting of SEQ ID NO: 1, SEQ NO: 2, SEQ ID NO: 3, SEQ ID NO: 4, and SEQ ID NO: 5.

2. A method for producing phloroglucinol, the method comprising:
   (i) contacting, with a suitable substrate, at least one polypeptide with phloroglucinol synthase activity, wherein the at least one polypeptide is a type III polyketide synthase of a bacteria of *Tsukamurella* genus, wherein the suitable substrate is a malonyl-CoA; and
   (ii) incubating the mixture resulting from step (i) under conditions suitable for producing phloroglucinol, wherein said polypeptide comprises an amino acid sequence having at least 95% identity with a sequence selected from the group consisting of SEQ ID NO: 1, SEQ NO: 2, SEQ ID NO: 3, SEQ ID NO: 4, and SEQ ID NO: 5.

3. The method according to claim 1, wherein said polypeptide comprises an amino acid sequence selected from the group consisting of SEQ ID NO: 1, SEQ NO: 2, SEQ ID NO: 3, SEQ ID NO: 4, and SEQ ID NO: 5.

4. The method according to claim 2, wherein said polypeptide comprises an amino acid sequence selected from the group consisting of SEQ ID NO: 1, SEQ NO: 2, SEQ ID NO: 3, SEQ ID NO: 4, and SEQ ID NO: 5.

5. The method according to claim 1, wherein the host cell is a microorganism selected from the group consisting of bacteria, yeast, fungi, algae and cyanobacteria.

6. The method according to claim 5, wherein the host cell is a yeast.

7. The method according to claim 6, wherein the yeast is of a genera selected from the group consisting of *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia* genera.

8. The method according to claim 7, wherein the yeast is from a species selected from the group consisting of *Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa* or *Torulaspora glabrata*.

9. The method according to claim 8, wherein the yeast is *Saccharomyces cerevisiae*.

10. The method according to claim 1, wherein the host cell comprises a nucleic acid molecule comprising a nucleic acid sequence encoding said polypeptide.

11. The method according to claim 10, wherein the nucleic acid molecule comprises a promoter controlling the expression of said nucleic acid sequence.

12. The method according to claim 11, wherein the promoter is exogenous.

13. The method according to claim 11, wherein the promoter is a yeast promoter.

14. The method according to claim 10, wherein the nucleic acid molecule comprises a terminator controlling the expression of said nucleic acid sequence.

15. The method according to claim 14, wherein the terminator is a yeast terminator.

16. The method according to claim 11, wherein the nucleic acid molecule comprises a terminator controlling the expression of said nucleic acid sequence.

17. The method according to claim 16, wherein the terminator is an exogenous terminator.

18. The method according to claim 16, wherein the terminator is a yeast terminator.

19. The method according to claim 10, wherein at least one copy of said nucleic acid molecule is integrated into the genome of said host cell.

20. The method according to claim 1, wherein the host cell comprises a vector, wherein the vector comprises a nucleic acid molecule comprising a nucleic acid sequence encoding said polypeptide.

* * * * *